US011633601B2

(12) United States Patent
Vervoordeldonk et al.

(10) Patent No.: US 11,633,601 B2
(45) Date of Patent: Apr. 25, 2023

(54) TREATMENT OF INFLAMMATORY DISORDERS

(71) Applicant: Galvani Bioelectronics Limited, Middlesex (GB)

(72) Inventors: Margarita J. Vervoordeldonk, Maarssen (NL); Robert Coatney, King of Prussia, PA (US); Cindy Cleypool, Middlesex (GB)

(73) Assignee: Galvani Bioelectronics Limited, Middlesex (GB)

( * ) Notice: Subject to any disclaimer, the term of this patent is extended or adjusted under 35 U.S.C. 154(b) by 0 days.

(21) Appl. No.: 16/955,282

(22) PCT Filed: Dec. 20, 2018

(86) PCT No.: PCT/GB2018/053727
§ 371 (c)(1),
(2) Date: Jun. 18, 2020

(87) PCT Pub. No.: WO2019/122904
PCT Pub. Date: Jun. 27, 2019

(65) Prior Publication Data
US 2020/0391036 A1    Dec. 17, 2020

Related U.S. Application Data

(60) Provisional application No. 62/608,426, filed on Dec. 20, 2017.

(51) Int. Cl.
*A61N 1/05* (2006.01)
*A61N 1/36* (2006.01)

(52) U.S. Cl.
CPC ....... *A61N 1/36121* (2013.01); *A61N 1/0556* (2013.01); *A61N 1/36139* (2013.01); *A61N 1/36178* (2013.01)

(58) Field of Classification Search
CPC .............. A61N 1/36121; A61N 1/0556; A61N 1/36139; A61N 1/36178
See application file for complete search history.

(56) References Cited

U.S. PATENT DOCUMENTS

2004/0236382 A1* 11/2004 Dinsmoor ................ A61N 1/05
607/40
2005/0075701 A1    4/2005 Shafer
(Continued)

FOREIGN PATENT DOCUMENTS

EP         1 897 586 A1    3/2008
WO    2012 083259 A2    6/2012
(Continued)

OTHER PUBLICATIONS

International Search Report and Written Opinion, PCT/GB2018/053727, dated Mar. 7, 2019, 14 pp.
(Continued)

*Primary Examiner* — Ankit D Tejani
*Assistant Examiner* — Joshua Brendon Solomon
(74) *Attorney, Agent, or Firm* — Banner & Witcoff, Ltd.

(57) ABSTRACT

Modulation of the neural activity of a nerve adjacent to the left gastro epiploic artery (LGEA) and/or a nerve adjacent to a short gastric artery (SGA) can modulate the neural activity
(Continued)

of the sympathetic nerves that impact splenic function. This is useful for reducing inflammation and providing ways of treating inflammatory disorders.

17 Claims, 17 Drawing Sheets

(56) References Cited

U.S. PATENT DOCUMENTS

| | | |
|---|---|---|
| 2005/0075702 A1 | 4/2005 | Shafer |
| 2009/0118780 A1* | 5/2009 | DiLorenzo ......... A61N 1/36114 607/2 |
| 2010/0125304 A1 | 5/2010 | Faltys |
| 2011/0106208 A1 | 5/2011 | Faltys et al. |
| 2011/0190849 A1 | 8/2011 | Faltys et al. |
| 2011/0313488 A1 | 12/2011 | Hincapie Ordonez et al. |
| 2013/0085537 A1 | 4/2013 | Mashiach |
| 2014/0288551 A1 | 9/2014 | Bharmi et al. |
| 2015/0174397 A1 | 6/2015 | Bhadra et al. |
| 2015/0343212 A1* | 12/2015 | Rousso .............. A61N 1/36007 607/40 |
| 2016/0015988 A1 | 1/2016 | Perryman et al. |
| 2016/0067497 A1 | 3/2016 | Levine et al. |
| 2017/0095679 A1 | 4/2017 | Sobotka et al. |
| 2018/0161577 A1* | 6/2018 | Goedeke .............. A61N 1/3627 |
| 2019/0290913 A1* | 9/2019 | Blancou ............ A61N 1/36171 |

FOREIGN PATENT DOCUMENTS

| | | |
|---|---|---|
| WO | 2014 153223 A1 | 9/2014 |
| WO | 2014 197625 A1 | 12/2014 |
| WO | 2016170510 A1 | 10/2016 |

OTHER PUBLICATIONS

Modin A., et al., "Repeated renal and splenic sympathetic nerve stimulation in anaesthetized pigs: maintained overflow of neuropeptide Y in controls but not after reserpine," J. Autonomic Nervous Systems, 49:2, Oct. 1, 1994, pp. 123-134.

Modin A., et al., "Comparison of the acute influence of neuropeptide Y and sympathetice stimulation on the composition of blood cells in the splenic vein in vivo," Regular Peptides, 47:2, Sep. 3, 1993, pp. 159-169.

Douglas B. McCreery et al., "Charge Density and Charge Per Phase as Cofactors in Neural Injury Induced by Electrical Stimulation," in IEEE Transactions on Biomedical Engineering, vol. 37, No. 10, pp. 996-1001, Oct. 1990, doi: 10.1109/10.102812.

Stuart F. Cogan et al., "Tissue damage thresholds during therapeutic electrical stimulation," Journal of Neural Engineering, Apr. 2016 ; 13(2): 021001. doi:10.1088/1741-2560/13/2/021001.

* cited by examiner

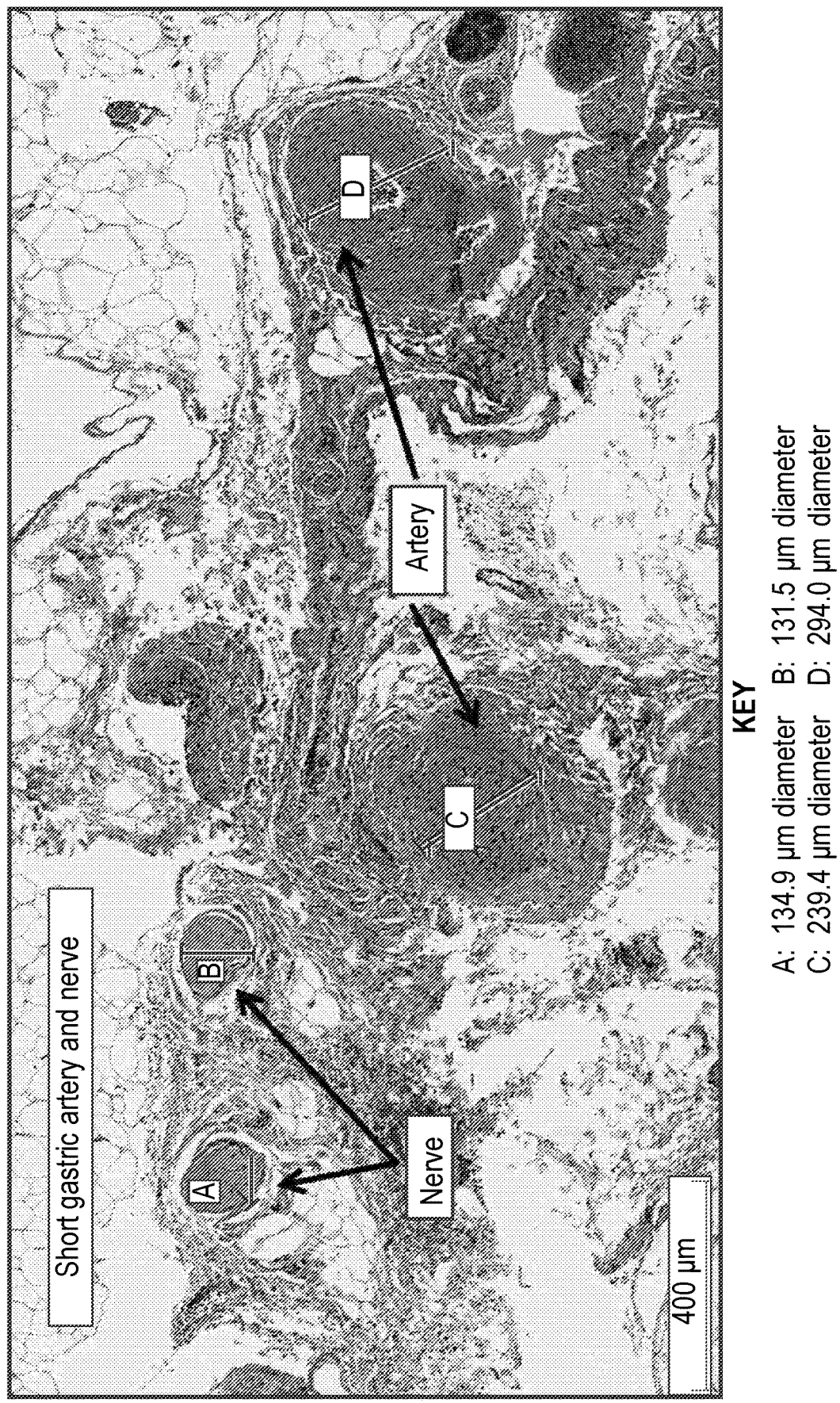

TREATMENT OF INFLAMMATORY DISORDERS

CROSS-REFERENCE TO RELATED APPLICATIONS

This application is a 371 of International Application No. PCT/GB2018/053727, filed Dec. 20, 2018, which claims priority to U.S. Provisional Application 62/608,426, filed Dec. 20, 2017, the contents of both of which are incorporated by reference herein in their entirety.

TECHNICAL FIELD

This invention relates to the treatment of inflammatory disorders, more particularly to methods and medical devices that deliver neuromodulatory therapy for such purposes.

BACKGROUND ART

Inflammation plays a fundamental role in host defenses and the progression of immune-mediated diseases (reviewed in [1]). The inflammatory response is initiated in response to an injury and/or an infection by chemical mediators (e.g. cytokines and prostaglandins) and inflammatory cells (e.g. leukocytes). A controlled inflammatory response is beneficial, for example, in the elimination of harmful agents and the initiation of the repair of damaged tissue providing protection against infection. However, the inflammatory response can become detrimental if dysregulated, leading to a variety of inflammatory disorders such as rheumatoid arthritis, psoriasis, osteoarthritis, asthma, allergies, septic shock syndrome, atherosclerosis, and inflammatory bowel disease, Crohn's disease, ulcerative colitis, and other clinical conditions mediated by chronic inflammation.

The spleen contains half of the body's monocyte population making this organ the main contributor in inflammation, in particular in response to endotoxemic shock [2] and, consequently, the target for septic shock therapy. This organ is known to be innervated by different nervous branches (reviewed in [3]). The parasympathetic innervation of the spleen is a matter of debate since Dale's isolation of acetylcholine (ACh) from the spleen [3]. Buijs and co-workers have suggested a parasympathetic innervation of the spleen in rodents [4,5], but human correlation to this nerve is not known. The traditional view of splenic innervation is proposed to be 98% sympathetic as demonstrated by neuroanatomical and neurochemical evidences [3].

From a functional point of view, vagus nerve stimulation (reviewed in [6]) as well as the nerve plexus surrounding the splenic artery (SA), referred to herein as the splenic arterial nerve, inhibit LPS-induced TNF release in mice [7]. According to Tracey and coworkers, the splenic arterial nerve activity is directly controlled by the cholinergic anti-inflammatory pathway (CAP) originating from the efferent branch of the vagus [6]. While vagal regulation of inflammatory tone and inflammatory reflex has received much attention, others have disputed the connections between vagus and splenic arterial nerve. Some authors have shown that denervation of the splenic arterial nerve in mice led to the inhibition of the CAP [7]. However, Martelli et al. have challenged this view by showing that the splenic arterial nerve was not directly connected to the vagus [8] but rather emerged as an independent branch of the greater splanchnic nerve which controls splenic arterial nerve activity [9,10]. These authors also counter the view that neural sensing of inflammatory markers is humoral and not neural [11]. Furthermore, it is disputed whether the efferent arm of the inflammatory reflex response is sympathetic or parasympathetic.

Electrostimulation of the vagus nerve has been shown to relieve symptoms of rheumatoid arthritis in a clinical trial [12]. However, there are concerns that stimulation of the vagus nerve can produce undesired, non-specific CNS effects because the vagus nerve is comprised predominantly of afferent fibers and innervates other tissues in addition to the spleen, including the heart, liver and gastrointestinal tract.

References [7], [13], [14] and [15] describe electrostimulation of the splenic arterial nerve. However, this approach is not ideal. This is because the SA is in close proximity to the pancreas and the nerve plexus surrounding the SA also innervates the pancreas and other structures, so stimulation of the splenic arterial nerve may be associated with surgical injury or damage to the pancreas and off-target effects. Furthermore, in most people, the splenic artery is tortuous, so it may be difficult to identify a consistent attachment site for electrode attachment for stimulation of the splenic arterial nerve.

Furthermore, the development of suitable neural interface for the splenic arterial nerve is challenging because there is significant movement of the artery due to pulsation which will likely affect electrode attachment in situ in the subject.

Thus, there is a need for further and improved ways of stimulating neural activity in splenic nerves, and in particular for treating inflammatory disorders.

SUMMARY OF THE INVENTION

The inventors have found a new way of stimulating splenic nerves with minimized surgical injury or damage to organs, such as the pancreas. This new way involves applying electrical signals to sympathetic fibers present in the gastrosplenic ligament and gastroepiploic arteries, such as the nerves that are adjacent to the short gastric arteries (SGAs) and the nerves that are adjacent to the left gastro epiploic artery (LGEA). The inventors have identified that stimulation of the neural activity of these nerves resulted in modulating splenic vascular tone in a manner that is equivalent to that seen with stimulation of the neural activity of the splenic plexus. For example, the data show that electrical signal application to these nerves in pigs resulted in a systemic reduction in TNFα, when blood collected from the pigs was exposed to an ex vivo endotoxin stimulation, lipopolysaccharide (LPS).

Furthermore, the data demonstrate that electrical signal application to these nerves resulted in a decrease in splenic blood flow and an increase in systolic pressure. The changes in the blood flow pattern are consistent with increased vascular resistance in the spleen. Thus, stimulation of the neural activity of these nerves is capable of stimulating the neural activity of the sympathetic nerves that impact splenic function. This is useful for reducing inflammation, particularly in disorders that are associated with inflammation, e.g. inflammatory disorders and/or immune-mediated inflammatory diseases (IMIDs).

Applying electrical signals to the sympathetic fibers present in the gastrosplenic ligament and gastroepiploic arteries, such as the nerves adjacent to the SGAs and the nerves adjacent to the LGEA, is more advantageous than apply electrical signals to the splenic arterial nerves (e.g. as described in 7,13,14,15) for at least the following reasons. In contrast to the SA, the LGEA and the SGAs are not in close proximity to the pancreas and are not critical for the blood supply to the pancreas, so surgical implantation of a device at or around the LGEA or the SGAs has a lower risk of surgical injury or damage to the pancreas or other organs/structures. Indeed, clinical procedures involving the removal of the gastrosplenic ligament (where the LGEA and SGAs are located) are common practice [16], and so any damages to these arteries would be expected have minimal adverse effects on the body. There may be possible reduction in off-target effects on solid organs (e.g. on pancreas and/or stomach), although this is yet to be characterized. Also, implantation of a device on or around the nerves adjacent to the LGEA and/or the nerves adjacent to a SGA involves a shorter clinical procedure compared to implanting a device on or around the nerves adjacent to the SA. Furthermore, whilst the SA is the main blood supply to the spleen, the LGEA and SGAs are part of the collateral circulation that goes to the spleen, and so any damages to the LGEA and SGAs are likely to have less profound effects on the perfusion of the spleen. In addition, the LGEA and SGAs have a smaller degree of movement with each pulsation compared to the SA because LGEA and SGAs are smaller in diameter, so neural interfacing elements near the LGEA and SGAs are less likely to affect neural interfacing element (e.g. electrode) attachment in situ in the subject.

Thus, the invention provides a method of reducing inflammation in a subject by reversibly modulating (e.g. stimulating) neural activity of a subject's nerve adjacent to the LGEA and/or a subject's nerve adjacent to a SGA. A preferred way of reversibly modulating (e.g. stimulating) the activity of the nerve uses a system which applies a signal to the nerve.

The invention provides a system for modulating neural activity in a subject's nerve adjacent to the LGEA and/or a subject's nerve adjacent to a SGA, the system comprising: at least one neural interfacing element, preferably an electrode, in signaling contact with the nerve adjacent to the LGEA and/or the nerve adjacent to the SGA, and a signal generator configured to generate at least one signal to be applied to the nerve via the at least one neural interfacing element such that the signal modulates the neural activity of the nerve to produce a change in a physiological parameter in the subject, wherein the change in the physiological parameter is one or more of the group consisting of: a reduction in a pro-inflammatory cytokine, an increase in an anti-inflammatory cytokine, an increase in a catecholamine, a change in an immune cell population, a change in an immune cell surface co-stimulatory molecule, a reduction in a factor involved in the inflammation cascade, a change in the level of an immune response mediator, a decrease in splenic blood flow and an increase in systemic blood pressure.

The invention also provides a system of the invention, comprising a detector (e.g. physiological sensor subsystem) configured for detecting one or more signals indicative of one or more physiological parameters; determining from the one or more signals one or more physiological parameters; determining the one or more physiological parameters indicative of worsening of the physiological parameter; and causing the signal to be applied to the nerve via the at least neural interfacing element, wherein the physiological parameter is one or more of the group consisting of: the level of a pro-inflammatory or an anti-inflammatory cytokine, the level of a catecholamine, the level of an immune cell population, the level of an immune cell surface co-stimulatory molecule, the level of a factor involved in the inflammation cascade, the level of an immune response mediator, splenic blood flow, and systemic blood pressure.

The invention also provides a method of treating an inflammatory disorder in a subject, comprising applying a signal to the subject's nerve adjacent to the LGEA and/or the subject's nerve adjacent to a SGA to reversibly modulate (e.g. stimulate) the neural activity of the nerve.

The invention also provides a method of treating an inflammatory disorder in a subject by reversibly modulating (e.g. stimulating) neural activity of the subject's nerve adjacent to the LGEA and/or the subject's nerve adjacent to a SGA, comprising: (i) implanting in the subject a system of the invention; (ii) positioning the neural interfacing element in signaling contact with the nerve; and optionally (iii) activating the system.

Similarly, the invention provides a method of reversibly modulating (e.g. stimulating) neural activity of a subject's nerve adjacent to the LGEA and/or a subject's nerve adjacent to a SGA, comprising: (i) implanting in the subject a system of the invention; (ii) positioning the neural interfacing element of the system in signaling contact with the nerve; and optionally (iii) activating the system.

The invention also provides a method of implanting a device or a system of the invention in a subject, comprising: positioning a neural interfacing element of the system in signaling contact with the nerve adjacent to the LGEA and/or the nerve adjacent to a SGA.

The invention also provides a method for treating an inflammatory disorder, comprising applying a signal to a subject's nerve adjacent to the LGEA and/or a subject's nerve adjacent to a SGA via at least one neural interfacing element, preferably an electrode, in signaling contact with the nerve, such that the signal reversibly modulates (e.g. stimulates) neural activity of the nerve to produce a change in a physiological parameter in the subject, wherein the change in the physiological parameter is one or more of the group consisting of: a reduction in a pro-inflammatory cytokine, an increase in an anti-inflammatory cytokine, an increase in a catecholamine, a change in an immune cell population, a change in an immune cell surface co-stimulatory molecule, a reduction in a factor involved in the inflammation cascade, a change in the level of an immune response mediator, a decrease in splenic blood flow, and an increase in systemic blood pressure.

The invention further provides an electrical waveform for use in reversibly modulating (e.g. stimulating) neural activity of a nerve adjacent to the LGEA and/or a nerve adjacent to a SGA in a subject, wherein the waveform is comprised of a plurality of pulse trains of square pulses, the plurality of pulse trains delivered at a frequency of between 1 Hz and 50 Hz, such that when applied to a subject's nerve, the waveform modulates (e.g. stimulates) neural activity in the nerve.

The invention also provides the use of a system for treating an inflammatory disorder in a subject, preferably in a subject who suffers from an inflammatory disorder, by reversibly modulating (e.g. stimulating) neural activity in the subject's nerve adjacent to the LGEA and/or the subject's nerve adjacent to a SGA.

The invention also provides a charged particle for use in a method of treating an inflammatory disorder, wherein the charged particle causes reversible depolarization of the nerve membrane of a nerve adjacent to the LGEA and/or a nerve adjacent to a SGA, such that an action potential is generated de novo in the modified nerve.

The invention also provides a modified nerve adjacent to the LGEA and/or a modified nerve adjacent to a SGA to which one or more neural interfacing elements of the system of the invention is attached, wherein the one or more neural interfacing element is in signaling contact with the nerve and so the nerve can be distinguished from the nerve in its natural state, and wherein the nerve is located in a patient who suffers from, or is at risk of, an inflammatory disorder.

The invention also provides a modified nerve adjacent to the LGEA and/or a modified nerve adjacent to a SGA, wherein the neural activity is reversibly modulated by applying a signal to the nerve.

The invention also provides a modified nerve adjacent to the LGEA and/or a modified nerve adjacent to a SGA, wherein the nerve membrane is reversibly depolarized by an electric field, such that an action potential is generated de novo in the modified nerve.

The invention also provides a modified nerve adjacent to the LGEA and/or a modified nerve adjacent to a SGA bounded by a nerve membrane, comprising a distribution of potassium and sodium ions movable across the nerve membrane to alter the electrical membrane potential of the nerve so as to propagate an action potential along the nerve in a normal state; wherein at least a portion of the nerve is subject to the application of a temporary external electrical field which modifies the concentration of potassium and sodium ions within the nerve, causing depolarization of the nerve membrane, thereby, in a disrupted state, temporarily generating an action potential de novo across that portion; wherein the nerve returns to its normal state once the external electrical field is removed.

The invention also provides a modified nerve adjacent to the LGEA and/or a modified nerve adjacent to a SGA obtainable by modulating (e.g. stimulating) neural activity of the nerve according to a method of the invention.

The invention also provides a method of modifying the neural activity of a subject's nerve adjacent to the LGEA and/or a subject's nerve adjacent to a SGA, comprising a step of applying a signal to the nerve in order to reversibly modulate (e.g. stimulate) the neural activity of the nerve in a subject.

Preferably the method does not involve a method for treatment of the human or animal body by surgery.

The subject already carries a system of the invention which is in signaling contact with the nerve.

The invention also provides a method of controlling a system of the invention which is in signaling contact with a subject's nerve adjacent to the LGEA and/or a subject's nerve adjacent to a SGA, comprising a step of sending control instructions to the system, in response to which the system applies a signal to the nerve.

The invention also provides a computer system implemented method, wherein the method comprises applying a signal to a subject's nerve adjacent to the LGEA and/or a subject's nerve adjacent to a SGA via at least one neural interfacing element, preferably an electrode, such that the signal reversibly modulates (e.g. stimulates) the neural activity of the nerve to produce a change in a physiological parameter in the subject, wherein the at least one neural interfacing element is suitable for placement on, in, or around the nerve, wherein the change in the physiological parameter is one or more of the group consisting of: a reduction in a pro-inflammatory cytokine, an increase in an anti-inflammatory cytokine, an increase in a catecholamine, a change in an immune cell population, a change in an immune cell surface co-stimulatory molecule, a reduction in a factor involved in the inflammation cascade, a change in the level of an immune response mediator, a decrease in splenic blood flow, and an increase in systemic blood pressure.

The invention also provides a computer comprising a processor and a non-transitory computer readable storage medium carrying an executable computer program comprising code portions which when loaded and run on the processor cause the processor to: apply a signal to a subject's nerve adjacent to the LGEA and/or a subject's nerve adjacent to a SGA via at least one neural interfacing element, preferably an electrode, such that the signal reversibly modulates (e.g. stimulates) the neural activity of the nerve to produce a change in a physiological parameter in the subject, wherein the at least one neural interfacing element is suitable for placement on, in, or around the nerve, wherein the change in the physiological parameter is one or more of the group consisting of: a reduction in a pro-inflammatory cytokine, an increase in an anti-inflammatory cytokine, an increase in a catecholamine, a change in an immune cell population, a change in an immune cell surface co-stimulatory molecule, a reduction in a factor involved in the inflammation cascade, a change in the level of an immune response mediator, a decrease in splenic blood flow, and an increase in systemic blood pressure.

DETAILED DESCRIPTION OF THE INVENTION

Nerves Adjacent to the LGEA and SGAs

Innervation of the spleen is primarily sympathetic or noradrenergic, with peptide neurons likely representing the bulk of the remaining neurons. The human spleen was traditionally considered to be innervated by the splenic plexus surrounding the splenic artery (SA) only. SA is covered with nervous tissue, which is derived from the coeliac plexus and continues with the SA to the spleen as the splenic plexus. The splenic plexus enters the spleen at the hilum where the SA diverges in terminal branches and the splenic plexus continues with these branches into the parenchyma of the spleen.

Interestingly, the inventors found that modulation (e.g. stimulation) of the neural activity of the nerves adjacent to the LGEA and the nerves adjacent to the SGAs are capable of stimulating the neural activity of sympathetic nerves that impact splenic function.

For example, the inventors have shown for the first time a neural connection between the nerves surrounding the SGA and LGEA, and the spleen (see example below). Surprisingly, it has been found that stimulation of the neural activity of these nerves results in changes in splenic arterial flow and changes in blood flow pattern that are consistent with increased vascular resistance in the spleen. This is consistent with the hypothesis that sympathetic fibers present in the gastrosplenic ligament and gastroepiploic arteries modulate splenic vascular tone in a manner that is equivalent to that seen with stimulation of the splenic plexus.

Furthermore, when neural activity of the nerves surrounding either the SGA or LGEA are stimulated, the neural activity in the splenic nerve along the hilum of the spleen increases This increase is. in a manner similar to that observed when the neural activity of the splenic artery neuro-vascular bundle is stimulated directly. Further, the decrease in splenic blood flow induced by stimulation of the neural activity of the nerves surrounding the LGEA and SGAs was abolished by cutting nerves at a site between the stimulating electrodes and the spleen. Further, cutting the LGEA nerve between the stimulating cuff and the spleen prevented the stimulation of induced decrease in splenic blood flow.

This would suggest that there is some communication between the spleen and these nerves.

Thus, the invention may involve modulating (e.g. stimulating) a nerve adjacent to the left gastro epiploic artery (LGEA). The invention may involve modulating (e.g. stimulating) a nerve adjacent to a short gastric artery (SGA). The invention may involve modulating (e.g. stimulating) both a nerve adjacent to the LGEA and a nerve adjacent to a SGA.

All human individuals contain a single LGEA (also known as the left gastro omental artery) and one or more SGAs. The number of SGAs may vary in individuals. For example, according the literature 4-5 SGAs [17] or 5-7 SGAs [18] may be present.

In humans, the LGEA and SGAs arise directly from the main trunk of the SA or from one of its terminal branches [17,19]. The SGAs and the LGEA are located in the gastrosplenic ligament, including their paravascular nervous tissue. The gastrosplenic ligament is a double fold of peritoneum running between the major curvature of the stomach and the spleen. The ligament consists of two layers of mesothelium.

The course of the SA, the SGAs and the LGEA in the upper abdomen are illustrated in FIG. 1, and explained further below.

Referring to FIG. 1A, which is a ventral view of splenic vascularization in relation to the stomach and pancreas, the SA originates from the coeliac trunk (CT), takes a peri-pancreatic course towards the spleen were eventually its terminal branches (TB) enter the splenic hilum. During its course pancreatic arteries (PAs) and SGAs branch off from the SA and respectively vascularize the pancreas and the upper part of the greater curvature of the stomach. At the hilum of the spleen, the SA continues as the LGEA which runs further along the greater curvature and anastomoses with the right gastroepiploic artery (RGEA). From the LGEA and the RGEA, small gastric arteries (SGAs) and omental arteries (OAs) emerge that respectively vascularize the stomach and greater omentum.

Referring to FIG. 1B, which is a transversal section through the upper abdomen illustrating the course of the SA and a SGA. The SA originates from the CT which in turn originates from the aorta. The SA takes a retroperitoneal and peri-pancreatic course towards the spleen. At its distal side the SA runs in the lienorenal (SR) ligament, a double fold of peritoneum (the latter is illustrated as a dashed lining). At the hilum TBs and SGAs branch off from the SA. The TBs enter the splenic tissue and the SGAs continue their course toward the stomach via the gastrosplenic (GS) ligament. At the hilum, a branch of the SA continues caudally as the LGEA (not visualized in this image). The LGEA runs in the caudal part of the GS ligament where after it continues in the greater omentum, which is a caudal continuation of the GS ligament.

The inventors found in cadaver studies that the average diameter of the proximal LGEA is about 0.2 cm (ranging from 0.15-0.28 cm), and its diameter is slightly reduced during its course in the greater omentum. On average, the LGEA originated about 9 cm (ranging from 8.1 cm to 12.5 cm) from the origin of the SA (see Study 1 below). The average amount of nerve bundles around the LGEA is 7 (ranging from 3 to 11 nerve bundles). The average diameter of nerve bundles around the LGEA is about 56 µm (ranging from 14-214 µm). It would be understood in the art that these measurements are obtained from formalin fixed specimens, so possible variations (e.g. ±5%) from these measurements may be seen in vivo. Furthermore, these measurements may vary amongst individuals.

The inventors found in cadaver studies that the average diameter of a SGA is about 0.15 cm (ranging from 0.08-0.4 cm). The average amount of SGAs branching from the SA was 3.33 (ranging from 1 to 6 SGAs) (see Study 1 below). The SGAs originated about 10 cm (ranging from 6.0 to 16.0 cm) from the origin of the SA, but this is dependent on the length of the SA (see Study 1 below). The average amount of nerve bundles around a SGA is 4.6 (ranging from 1 to 8 nerve bundles). The average mean diameter of nerve bundles around a SGA is about 55 µm (ranging from 12-173 µm). It would be understood in the art that these measurements are obtained from formalin fixed specimens, so possible variations (e.g. ±5%) from these measurements may be seen in vivo. Furthermore, these measurements may vary amongst individuals.

Some literature describes that the SGAs may also originate from the LGEA [18], but to make a clear distinction, the branches originating from the LGEA going to the stomach are referred to herein as the gastric branches (GBs).

In some embodiments, the invention involves modulating the neural activity of a nerve adjacent to the LGEA or a nerve adjacent to SGA. Preferably, the invention involves modulating the neural activity of the nerve adjacent to the SGA. The SGA is more easily accessible surgically compared to the LGEA.

The LGEA and the SGA are more easily accessible surgically than the splenic artery.

Although in principle the invention can apply a signal to modulate neural activity at any point along a nerve adjacent to the LGEA or a SGA, the signal application site is preferably in the gastrosplenic ligament (see example below).

The signal application site for the nerve adjacent to the LGEA may be at the proximal part of the nerve near the spleen.

The signal application site for the nerve adjacent to a SGA may be at the proximal part of the nerve near the spleen.

In embodiments involving modulating (e.g. stimulating) the neural activity of both the nerve adjacent to the LGEA and the nerve adjacent to a SGA, the signals may be applied to the nerves simultaneously or sequentially.

The signal may be applied at multiple sites along a nerve adjacent to the LGEA.

The signal may be applied at multiple sites along a nerve adjacent to the SGA.

The signal may be applied at multiple nerves adjacent to multiple SGAs. The signal may be applied at multiple sites along multiple nerves adjacent to multiple SGAs.

Where the invention refers to a modified nerve adjacent to the LGEA and/or a modified nerve adjacent to a SGA, this nerve is ideally present in situ in a subject.

Modulation of Neural Activity

The invention involves modulation of neural activity of a nerve adjacent to the LGEA and/or a nerve adjacent to the SGA. As used herein, "neural activity" of a nerve means the signaling activity of the nerve, for example the amplitude, frequency and/or pattern of action potentials in the nerve. The term "pattern", as used herein in the context of action potentials in the nerve, is intended to include one or more of: local field potential(s), compound action potential(s), aggregate action potential(s), and also magnitudes, frequencies, areas under the curve and other patterns of action potentials in the nerve or sub-groups (e.g. fascicules) of neurons therein.

Modulation of neural activity, as used herein, is taken to mean that the signaling activity of the nerve is altered from the baseline neural activity—that is, the signaling activity of the nerve in the subject prior to any intervention. Modulation may involve creation of action potentials in the nerve compared to baseline activity. The modulation of the nerve according to the present invention results in preferential increased sympathetic signals to the spleen.

The invention preferentially stimulates the neural activity of the nerve. Stimulation may result in at least part of the nerve being increased compared to baseline neural activity in that part of the nerve. This increase in activity can be across the whole nerve, in which case neural activity is increased across the whole nerve. Stimulation may apply to both efferent fibers and afferent fibers of the nerve. In some embodiments, stimulation may apply only to efferent fibers. The inventors found that the nerves adjacent to the LGEA and the SGAs contain no or minimal afferent fibers.

Stimulation typically involves increasing neural activity e.g. generating action potentials beyond the point of the stimulation in at least a part of the nerve. At any point along the axon, a functioning nerve will have a distribution of potassium and sodium ions across the nerve membrane. The distribution at one point along the axon determines the electrical membrane potential of the axon at that point, which in turn influences the distribution of potassium and sodium ions at an adjacent point, which in turn determines the electrical membrane potential of the axon at that point, and so on. This is a nerve operating in its normal state, wherein action potentials propagate from point to adjacent point along the axon, and which can be observed using conventional experimentation.

One way of characterizing a stimulation of neural activity is a distribution of potassium and sodium ions at one or more points in the axon, which is created not by virtue of the electrical membrane potential at adjacent a point or points of the nerve as a result of a propagating action potential, but by virtue of the application of a temporary external electrical field. The temporary external electrical field artificially modifies the distribution of potassium and sodium ions within a point in the nerve, causing depolarization of the nerve membrane that would not otherwise occur. The depolarization of the nerve membrane caused by the temporary external electrical field generates de novo action potential across that point. This is a nerve operating in a disrupted state, which can be observed by a distribution of potassium and sodium ions at a point in the axon (the point which has been stimulated) that has an electrical membrane potential that is not influenced or determined by the electrical membrane potential of an adjacent point.

Stimulation of neural activity is thus understood to be increasing neural activity beyond the point of signal application. Thus, the nerve at the point of signal application is modified in that the nerve membrane is reversibly depolarized by an electric field, such that a de novo action potential is generated and propagates through the modified nerve. Hence, the nerve at the point of signal application is modified in that a de novo action potential is generated.

When an electrical signal is used with the invention, the stimulation is based on the influence of electrical currents (e.g. charged particles, which may be one or more electrons in an electrode attached to the nerve, or one or more ions outside the nerve or within the nerve, for instance) on the distribution of ions across the nerve membrane.

Stimulation of neural activity encompasses full stimulation of neural activity in the nerve—that is, embodiments where the total neural activity is increased in the whole nerve.

Stimulation of neural activity may be partial stimulation. Partial stimulation may be such that the total signaling activity of the whole nerve is partially increased, or that the total signaling activity of a subset of nerve fibers of the nerve is fully increased (i.e. there is no neural activity in that subset of fibers of the nerve), or that the total signaling of a subset of nerve fibers of the nerve is partially increased compared to baseline neural activity in that subset of fibers of the nerve. For example, an increase in neural activity of ≤5%, ≤10%, ≤15%, ≤20%, ≤25%, ≤30%, ≤35%, ≤40%, ≤45%, ≤50%, ≤60%, ≤70%, ≤80%, ≤90% or ≤95%, or an increase of neural activity in a subset of nerve fibers of the nerve. The neural activity may be measured by methods known in the art, for example, by the number of action potentials which propagate through the axon and/or the amplitude of the local field potential reflecting the summed activity of the action potentials.

The invention may selectively stimulate nerve fibers of various sizes within a nerve. Larger nerve fibers tend to have a lower threshold for stimulation than smaller nerve fibers. Thus, for example, increasing signal amplitude (e.g. increasing amplitude of an electric signal) may generate stimulation of the smaller fibers as well as larger fibers. For example, asymmetrical (triangular instead of square pulse) waveforms may be used stimulate C-fibers (unmyelinated).

Modulation of neural activity may be an alteration in the pattern of action potentials. It will be appreciated that the pattern of action potentials can be modulated without necessarily changing the overall frequency or amplitude. For example, modulation of neural activity may be such that the pattern of action potentials is altered to more closely resemble a healthy state rather than a disease state.

Modulation of neural activity may comprise altering the neural activity in various other ways, for example increasing or decreasing a particular part of the neural activity and/or stimulating new elements of activity, for example: in particular intervals of time, in particular frequency bands, according to particular patterns and so forth.

Modulation of neural activity may be (at least partially) corrective. As used herein, "corrective" is taken to mean that the modulated neural activity alters the neural activity towards the pattern of neural activity in a healthy subject, and this is called axonal modulation therapy. That is, upon cessation of signal application, neural activity in the nerve more closely resembles (ideally, substantially fully resembles) the pattern of action potentials in the nerve observed in a healthy subject than prior to signal application. Such corrective modulation can be any modulation as defined herein. For example, application of a signal may result in an increase on neural activity, and upon cessation of signal application the pattern of action potentials in the nerve resembles the pattern of action potentials observed in a healthy subject. By way of further example, application of the signal may result in neural activity resembling the pattern of action potentials observed in a healthy subject and, upon cessation of the signal, the pattern of action potentials in the nerve remains the pattern of action potentials observed in a healthy subject.

One advantage of the invention is that modulation of neural activity is reversible. Hence, the modulation of neural activity is not permanent. For example, upon cessation of the application of a signal, neural activity in the nerve returns substantially towards baseline neural activity within 1-60 seconds, or within 1-60 minutes, or within 1-24 hours (e.g. within 1-12 hours, 1-6 hours, 1-4 hours, 1-2 hours), or within 1-7 days (e.g. 1-4 days, 1-2 days). In some instances of reversible modulation, the neural activity returns substantially fully to baseline neural activity. That is, the neural activity following cessation of the application of a signal is substantially the same as the neural activity prior to a signal being applied. Hence, the nerve or the portion of the nerve has regained its normal physiological capacity to propagate action potentials.

In other embodiments, modulation of the neural activity may be substantially persistent. As used herein, "persistent" is taken to mean that the modulated neural activity has a prolonged effect. For example, upon cessation of the application of a signal, neural activity in the nerve remains substantially the same as when the signal was being applied—i.e. the neural activity during and following signal application is substantially the same. Reversible modulation is preferred.

Inflammatory Disorders

The invention is useful for treating conditions associated with an imbalance of pro- and anti-inflammatory cytokine profiles compared to the physiological homeostatic state, such as inflammatory disorders (e.g. chronic inflammatory disorders).

Inflammatory disorders are typically characterized by an imbalance of pro- and anti-inflammatory cytokine profiles compared to the normal physiological homeostatic state, e.g. increased pro-inflammatory cytokines levels and/or decreased anti-inflammatory cytokines levels compared to the normal physiological homeostatic state.

Thus, the invention is useful for treating subjects suffering from, or are at risk in developing, inflammatory disorders. The invention may treat or ameliorate the effects of the inflammatory disorders by reducing inflammation. This may be achieved by decreasing the production and release of pro-inflammatory cytokines, and/or increasing the production and release of anti-inflammatory cytokines, from the spleen by reversibly electrically stimulating the nerve.

Inflammatory disorders include autoimmune disorders, such as arthritis (e.g. rheumatoid arthritis, osteoarthritis, psoriatic arthritis), Grave's disease, myasthenia gravis, thryoiditis, systemic lupus erythematosus, Goodpasture's syndrome, Behcets's syndrome, allograft rejection, graft-versus-host disease, ankylosing spondylitis, Berger's disease, diabetes including Type I diabetes, Reitier's syndrome, spondyloarthropathy psoriasis, multiple sclerosis, Inflammatory Bowel Disease, Crohn's disease, Addison's disease, autoimmune mediated hair loss (e.g., alopecia areata) and ulcerative colitis.

Certain examples of inflammatory disorders include diseases involving the gastrointestinal tract and associated tissues, such as appendicitis, peptic, gastric and duodenal ulcers, peritonitis, pancreatitis, ulcerative, pseudomembranous, acute and ischemic colitis, inflammatory bowel disease, diverticulitis, cholangitis, cholecystitis, Crohn's disease, Whipple's disease, hepatitis, abdominal obstruction, volvulus, post-operative ileus, ileus, celiac disease, periodontal disease, pernicious anemia, amebiasis and enteritis.

Further examples of inflammatory disorders include diseases of the bones, joints, muscles and connective tissues, such as the various arthritides and arthralgias, osteomyelitis, gout, periodontal disease, rheumatoid arthritis, spondyloarthropathy, ankylosing spondylitis and synovitis.

Further examples include systemic or local inflammatory diseases and conditions, such as asthma, allergy, anaphylactic shock, immune complex disease, sepsis, septicemia, endotoxic shock, eosinophilic granuloma, granulomatosis, organ ischemia, reperfusion injury, organ necrosis, hay fever, cachexia, hyperoxia, septic abortion, HIV infection, herpes infection, organ transplant rejection, disseminated bacteremia, Dengue fever, malaria and sarcoidosis.

Other examples include diseases involving the urogenital system and associated tissues, such as diseases that include epididymitis, vaginitis, orchitis, urinary tract infection, kidney stone, prostatitis, urethritis, pelvic inflammatory bowel disease, contrast induced nephropathy, reperfusion kidney injury, acute kidney injury, infected kidney stone, herpes infection, and candidiasis.

Further examples are dermatological diseases and conditions of the skin (such as burns, dermatitis, dermatomyositis, burns, cellulitis, abscess, contact dermatitis, dermatomyositis, warts, wheal, sunburn, urticaria warts, and wheals); diseases involving the cardiovascular system and associated tissues, (such as myocardial infarction, cardiac tamponade, vasulitis, aortic dissection, coronary artery disease, peripheral vascular disease, aortic abdominal aneurysm, angiitis, endocarditis, arteritis, atherosclerosis, thrombophlebitis, pericarditis, myocarditis, myocardial ischemia, congestive heart failure, periarteritis nodosa, and rheumatic fever, filariasis thrombophlebitis, deep vein thrombosis); as well as various cancers, tumors and proliferative disorders (such as Hodgkin's disease), nosocomial infection; and, in any case the inflammatory or immune host response to any primary disease.

Other examples of inflammatory disorders include diseases involving the central or peripheral nervous system and associated tissues, such as Alzheimer's disease, depression, multiple sclerosis, cerebral infarction, cerebral embolism, carotid artery disease, concussion, subdural hematoma, epidural hematoma, transient ischemic attack, temporal arteritis, spinal cord injury without radiological finding (SCI-WORA), cord compression, meningitis, encephalitis, cardiac arrest, Guillain-Barre, spinal cord injury, cerebral venous thrombosis and paralysis.

Conditions associated with a particular organ such as eye or ear may also include an immune or inflammatory response such as conjunctivitis, iritis, glaucoma, episcleritis, acute retinal occlusion, rupture globe, otitis media, otitis externa, uveitis and Meniere's disease.

Another example of an inflammatory disorder is post-operative ileus (POI). POI is experienced by the vast majority of patients undergoing abdominal surgery. POI is characterized by transient impairment of gastro-intestinal (GI) function along the GI tract as well pain and discomfort to the patient and increased hospitalization costs.

The impairment of GI function is not limited to the site of surgery, for example, patients undergoing laparotomy can experience colonic or ruminal dysfunction. POI is at least in part mediated by enhanced levels of pro-inflammatory cytokines and infiltration of leukocytes at the surgical site. Neural inhibitory pathways activated in response to inflammation contribute to the paralysis of secondary GI organs distal to the site of surgery. Stimulation of neural activity as taught herein may thus be effective in the treatment or prevention of POI.

The invention is particularly useful in treating autoimmune disorders (e.g. rheumatoid arthritis, osteoarthritis, psoriatic arthritis, spondyloarthropathy, ankylosing spondylitis, psoriasis, systemic lupus erythematosus (SLE), multiple sclerosis, Inflammatory Bowel Disease, Crohn's disease, and ulcerative colitis) and sepsis.

This invention is particularly useful for treating B cell mediated autoimmune disorders (e.g. systemic lupus erythematosus (SLE) and rheumatoid arthritis (RA)).

The invention is particularly useful for treating inflammatory conditions associated with bacterial infections. For example, the invention is particularly useful for treating inflammatory conditions caused or exacerbated by *Escherichia coli, Staphylococcus aureus, Pneumococcus, Haemophilus influenza, Neisseria meningitides, Streptococcus* pneumonia, Methicillin-resistant *Staphylococcus aureus* (MRSA), *Klebsiella* or *Enterobacter* infection.

Treatment of an inflammatory disorder can be assessed in various ways, but typically involves determining an improvement in one or more physiological parameters of the subject.

Useful physiological parameters of the invention may be one or more of the group consisting of: the level of a pro-inflammatory cytokine, the level of an anti-inflammatory cytokine, the level of a catecholamine, the level of an immune cell population, the level of an immune cell surface co-stimulatory molecule, the level of a factor involved in the inflammation cascade, the level of an immune response mediator, splenic blood flow, and systemic blood pressure.

As used herein, an "improvement in a determined physiological parameter" is taken to mean that, for any given physiological parameter, an improvement is a change in the value of that parameter in the subject towards the normal value or normal range for that value—i.e. towards the expected value in a healthy subject. As used herein, "worsening of a determined physiological parameter" is taken to mean that, for any given physiological parameter, worsening is a change in the value of that parameter in the subject away from the normal value or normal range for that value—i.e. away from the expected value in a healthy subject.

Improvement in a determined physiological parameter according to the invention is indicated by one or more of the group consisting of: a reduction in a pro-inflammatory cytokine, an increase in an anti-inflammatory cytokine, an increase in a catecholamine, a change in an immune cell population, a change in an immune cell surface co-stimulatory molecule, a reduction in a factor involved in the inflammation cascade, a change in the level of an immune response mediator, a decrease in blood flow, and an increase in systemic blood pressure. The invention might not lead to a change in all of these parameters.

By stimulating a nerve adjacent to the LGEA and/or a nerve adjacent to the SGA according to the invention, the spleen may: (a) decrease the secretion of a pro-inflammatory cytokine compared to baseline secretion; and/or (b) increase the secretion of an anti-inflammatory cytokine compared to baseline secretion. For example, the decrease in a pro-inflammatory cytokine secretion may be by: ≤5%, ≤10%, ≤15%, ≤20%, ≤25%, ≤30%, ≤35%, ≤40%, ≤45%, ≤50%, ≤60%, ≤70%, ≤80%, ≤90% or ≤95%. The increase in an anti-inflammatory cytokine secretion may be by: ≤5%, ≤10%, ≤15%, ≤20%, ≤25%, ≤30%, ≤35%, ≤40%, ≤45%, ≤50%, ≤60%, ≤70%, ≤80%, ≤90%, ≤95%, ≤100%, ≤150% or ≤200%.

Once the cytokine is secreted into the circulation, its concentration in circulation is diluted. Stimulation of the nerve may result in: (a) a decrease in the level of a pro-inflammatory cytokine in the plasma or serum by ≤5%, ≤10%, ≤15%, ≤20%, ≤25%, ≤30%, ≤35%, ≤40%, ≤45%, ≤50%, ≤60%, ≤70%, ≤80%, ≤90%, or ≤95%; and/or (b) an increase in the level of an anti-inflammatory cytokine in the plasma or serum by ≤5%, ≤10%, ≤15%, ≤20%, ≤25%, ≤30%, ≤35%, ≤40%, ≤45%, ≤50%, ≤60%, ≤70%, ≤80%, ≤90%, ≤95%, ≤100%, ≤150% or ≤200%. Preferably the cytokine level in the serum is measured.

By stimulating a nerve adjacent to the LGEA and/or a nerve adjacent to the SGA according to the invention, the level of catecholamine (e.g. norepinephrine or epinephrine), e.g. its level in the spleen in the spleen, may increase, for example, by: ≤5%, ≤10%, ≤15%, ≤20%, ≤25%, ≤30%, ≤35%, ≤40%, ≤45%, ≤50%, ≤60%, ≤70%, ≤80%, ≤90%, ≤95%, ≤100%, ≤150% or ≤200%.

For example, the inventors found that stimulating a nerve adjacent to the LGEA and/or SGA can decrease the level of a pro-inflammatory cytokine (e.g. TNFα) in the serum by 30%-60% (see Study 2 below).

Pro-inflammatory cytokines are known in the art. Examples of these include tumor necrosis factor (TNF; also known as TNFα or cachectin), interleukin (IL)-1α, IL-1β, IL-2; IL-5, IL-6, IL-8, IL-15, IL-18, interferon γ (IFN-γ); platelet-activating factor (PAF), thromboxane; soluble adhesion molecules; vasoactive neuropeptides; phospholipase A2; plasminogen activator inhibitor (PAI-1); free radical generation; neopterin; CD14; prostacyclin; neutrophil elastase; protein kinase; monocyte chemotactic proteins 1 and 2 (MCP-1, MCP-2); macrophage migration inhibitory factor (MIF), high mobility group box protein 1 (HMGB-1), and other known factors.

Anti-inflammatory cytokines are also known in the art. Examples of these include IL-4, IL-10, IL-17, IL-13, IL-1α, and TNFα receptor.

It will be recognized that some of pro-inflammatory cytokines may act as anti-inflammatory cytokines in certain circumstances, and vice-versa. Such cytokines are typically referred to as pleiotropic cytokines.

Factors involved in immune responses may be useful measurable parameters for the invention, for example, TGF, PDGF, VEGF, EGF, FGF, I-CAM, nitric oxide.

Chemokines may also be useful measurable parameters for the invention, such as 6cKine and MIP3beta, and chemokine receptors, including CCR7 receptor.

Changes in immune cell population (Langerhans cells, dendritic cells, lymphocytes, monocytes, macrophages), or immune cell surface co-stimulatory molecules (Major Histocompatibility, CD80, CD86, CD28, CD40) may also be useful measurable parameters for the invention.

Factors involved in the inflammatory cascade may also be useful measurable parameters for the invention. For example, the signal transduction cascades include factors such as NFκ-B, Egr-1, Smads, toll-like receptors, and MAP kinases.

Methods of assessing these physiological parameters are known in the art. Detection of any of the measurable parameters may be done before, during and/or after modulation of neural activity in the nerve.

For example, a cytokine, chemokine, or a catecholamine (e.g. norepinephrine or epinephrine) may be directly detected, e.g. by ELISA. Alternatively, the presence or amount of a nucleic acid, such as a polyribonucleotide, encoding a polypeptide described herein may serve as a measure of the presence or amount of the polypeptide. Thus, it will be understood that detecting the presence or amount of a polypeptide will include detecting the presence or amount of a polynucleotide encoding the polypeptide.

Quantitative changes of the biological molecules (e.g. cytokines) can be measured in a living body sample such as urine or plasma. Detection of the biological molecules may be performed directly on a sample taken from a subject, or the sample may be treated between being taken from a subject and being analyzed. For example, a blood sample may be treated by adding anti-coagulants (e.g. EDTA), followed by removing cells and cellular debris, leaving plasma containing the relevant molecules (e.g. cytokines) for analysis. Alternatively, a blood sample may be allowed to coagulate, followed by removing cells and various clotting factors, leaving serum containing the relevant molecules (e.g. cytokines) for analysis.

In the embodiments where the signal is applied whilst the subject is asleep, the invention may involve determining the subject's circadian rhythm phase markers, such as the level of cortisol (or its metabolites thereof), the level of melatonin (or its metabolites thereof) or core body temperature.

Cortisol or melatonin levels can be measured in the blood (e.g. plasma or serum), saliva or urine.

Methods of determining the levels of these markers are known in the art, e.g. by enzyme-linked immunosorbent assay (ELISA) or radioimmunoassay. If measurements of the subject's circadian rhythm phase markers indicate circadian oscillations of inflammatory markers which may beneficially be regulated by application of a signal with a system of the invention, then application of the signal at night at a suitable periodicity according to the subject's circadian rhythm may be appropriate.

As used herein, a physiological parameter is not affected by the modulation (e.g. stimulation) of the neural activity if the parameter does not change (in response to nerve modulation) from the normal value or normal range for that value of that parameter exhibited by the subject or subject when no intervention has been performed i.e. it does not depart from the baseline value for that parameter. Such a physiological parameter may be arterial blood pressure or glucose metabolism. Suitable methods for determining changes in any these physiological parameters would be appreciated by the skilled person.

The skilled person will appreciate that the baseline for any neural activity or physiological parameter in an subject need not be a fixed or specific value, but rather can fluctuate within a normal range or may be an average value with associated error and confidence intervals. Suitable methods for determining baseline values are well known to the skilled person.

As used herein, a physiological parameter is determined in a subject when the value for that parameter exhibited by the subject at the time of detection is determined. A detector (e.g. a physiological sensor subsystem, a physiological data processing module, a physiological sensor, etc.) is any element able to make such a determination.

Thus, in certain embodiments, the invention further comprises a step of determining one or more physiological parameters of the subject, wherein the signal is applied only when the determined physiological parameter meets or exceeds a predefined threshold value. In such embodiments wherein more than one physiological parameter of the subject is determined, the signal may be applied when any one of the determined physiological parameters meets or exceeds its threshold value, alternatively only when all of the determined physiological parameters meet or exceed their threshold values. In certain embodiments wherein the signal is applied by a system of the invention, the system further comprises at least one detector configured to determine the one or more physiological parameters of the subject.

In certain embodiments, the physiological parameter is an action potential or pattern of action potentials in a nerve of the subject, wherein the action potential or pattern of action potentials is associated with the condition that is to be treated.

It will be appreciated that any two physiological parameters may be determined in parallel embodiments, the controller is coupled detect the pattern of action potentials tolerance in the subject.

A predefined threshold value for a physiological parameter is the minimum (or maximum) value for that parameter that must be exhibited by a subject or subject before the specified intervention is applied.

For any given parameter, the threshold value may be defined as a value indicative of a pathological state or a disease state. The threshold value may be defined as a value indicative of the onset of a pathological state or a disease state. Thus, depending on the predefined threshold value, the invention can be used as a treatment. Alternatively, the threshold value may be defined as a value indicative of a physiological state of the subject (that the subject is, for example, asleep, post-prandial, or exercising). Appropriate values for any given physiological parameter would be simply determined by the skilled person (for example, with reference to medical standards of practice).

Such a threshold value for a given physiological parameter is exceeded if the value exhibited by the subject is beyond the threshold value—that is, the exhibited value is a greater departure from the normal or healthy value for that physiological parameter than the predefined threshold value.

A subject of the invention may, in addition to having a system according to the invention, receive medicine for their condition. For instance, a subject having a system according to the invention may receive an anti-inflammatory medicine (which will usually continue medication which was occurring before receiving the implant). Such medicines include, nonsteroidal anti-inflammatory drugs (NSAIDs), steroids, 5ASAs, disease-modifying-anti-inflammatory drugs (DMARDs) such as azathioprine, methotrexate and cyclosporin, biological drugs like infliximab and adalimumab, and the new oral DMARDs-like Jak inhibitors. Thus the invention provides the use of these medicines in combination with a system of the invention.

A System for Implementing the Invention

A system according to the invention comprises a device, the device may be implantable (e.g. implantable device 106 of FIG. 2). The implantable device comprises at least one neural interface 108 comprising a neural interfacing element, preferably an electrode (e.g. electrode 109), suitable for placement on or around a nerve adjacent to the LGEA and/or a nerve adjacent to a SGA. The system preferably also comprises a processor (e.g. microprocessor 113) coupled to the at least one neural interfacing element.

The at least one neural interfacing element may take many forms, and includes any component which, when used in an implantable system for implementing the invention, is capable of applying a stimulus or other signal that modulates electrical activity, e.g., action potentials, in a nerve.

The various components of the system are preferably part of a single physical device, either sharing a common housing or being a physically separated collection of interconnected components connected by electrical leads (e.g. leads 107). As an alternative, however, the invention may use a system in which the components are physically separate, and communicate wirelessly. Thus, for instance, the at least one neural interfacing element (e.g. electrode 109) and the implantable device (e.g. implantable device 106) can be part of a unitary device, or together may form an system (e.g. system 116). In both cases, further components may also be present to form a wider system (e.g. system 100).

Suitable Forms of a Signal

The invention uses a signal applied via one or more neural interfacing elements (e.g. electrode 109) placed in signaling contact with a nerve adjacent to the LGEA and/or a nerve adjacent to a SGA, preferably on or around the nerve.

Signals applied according to the invention are ideally non-destructive. As used herein, a "non-destructive signal" is a signal that, when applied, does not irreversibly damage the underlying neural signal conduction ability of the nerve. That is, application of a non-destructive signal maintains the ability of the nerve or fibers thereof, or other nerve tissue to which the signal is applied, to conduct action potentials when application of the signal ceases, even if that conduction is in practice artificially stimulated as a result of application of the non-destructive signal.

The signal will usually be an electrical signal, which may be, for example, a voltage or current waveform. The at least one neural interfacing element (e.g. electrode 109) of the system (e.g. system 116) is configured to apply the electrical signals to a nerve, or a part thereof. However, electrical signals are just one way of implementing the invention, as is further discussed below.

An electrical signal can take various forms, for example, a voltage or current. In certain such embodiments the signal applied comprises a direct current (DC), such as a charge-balanced DC, or a charged-balance alternating current (AC) waveform, or both a DC and an AC waveform. As used herein, "charge-balanced" in relation to a DC current is taken to mean that the positive or negative charge introduced into any system (e.g. a nerve) as a result of a DC current being applied is balanced by the introduction of the opposite charge in order to achieve overall (net) neutrality. In other words, a charge-balance DC current includes a cathodic pulse and an anodic pulse.

The signal may be applied continuously or periodically, and/or episodically, as is further discussed below. Hence, the signal may be applied: (i) continuously, (ii) periodically, (iii) episodically, (iv) continuously and episodically, or (iv) periodically and episodically.

The electric signal may be applied with a step change or with a ramp change in current or intensity.

Particular signal parameters for modulating (e.g. stimulating) a nerve adjacent to the LGEA and/or a nerve adjacent to a SGA are further described below. Modulation of the neural activity of the nerve can be achieved using electrical signals which serve to replicate the normal neural activity of the nerve.

With reference again to FIG. 2, the system 116 comprises an implantable device 106 which may comprise a signal generator 117; for example, a pulse generator. When the implantable device comprises a pulse generator, the implantable device 106 may be referred to as an implantable pulse generator. The signal generator 117 may also be a voltage or current source. The signal generator 117 may be pre-programmed to deliver one or more pre-defined waveforms with signal parameters falling within the range given below. Alternatively, the signal generator 117 may be controllable to adjust one or more of the signal parameters described further below. Control may be open loop, wherein the operator of the implantable device 106 may configure the signal generator using an external controller (e.g. controller 101), or control may be closed loop, wherein signal generator modifies the signal parameters in response to one or more physiological parameters of the subject, as is further described below.

Signal Parameters

In all of the above examples, the signal generator 117 may be configured to deliver an electrical signal to modulate (e.g. stimulate) a nerve adjacent to the LGEA and/or a nerve adjacent to a SGA. For example, the signal generator 117 is configured to apply an electrical signal with certain electrical signal parameters to stimulate neural activity in the nerve. Signal parameters for stimulating neural activity in the nerve, which are described in detail below, may include waveform, amplitude, and frequency.

The signal parameters described herein are applicable independently to the signal to be applied to a nerve adjacent to the LGEA or to the signal to be applied to a nerve adjacent to a SGA.

Waveform

Modulation (e.g. stimulation) of a nerve adjacent to the LGEA and/or a nerve adjacent to a SGA can be achieved using electrical signals which serve to replicate the normal neural activity of the nerve.

Thus, the waveform of the electrical signal comprises one or more pulse trains, each with a defined pulse width. The pulses are preferably square pulses. Other pulse waveforms such as sawtooth, sinusoidal, triangular, trapezoidal, quasi-trapezodial or complex waveforms may also be used with the invention.

Some embodiments of the signal comprise a plurality of temporally separated pulse trains, each pulse train being made up of a plurality of pulses.

The pulses may have a pulse width between 250 and 1000 µs, preferably between 400 and 1000 µs (including, if applicable, both positive and negative phases of the pulse, in the case of a charge-balanced biphasic pulse). For example, the pulse width may be ≤500 µs, ≤600 µs, ≤700 µs, ≤800 µs, ≤900 µs, or ≤1000 µs. Additionally or alternatively, the pulse width may be ≥400 µs, ≥500 µs, ≥600 µs, ≥700 µs, ≥800 µs, or ≥900 µs. Any combination of the upper and lower limits above is also possible. The pulse width may additionally be limited by the frequency.

The pulses may be charge-balanced. A charge-balanced pulse refers to a pulse which, over the period of the pulse, applies equal amounts (or thereabouts) of positive and negative charge to the nerve.

In some embodiments, the pulses are biphasic pulses. The term "biphasic" refers to a signal which delivers to the nerve over time both a positive and negative charge. The biphasic pulses are preferably charge-balanced. The term "charge-balanced" in relation to a pulse train is taken to mean that the positive charge and negative charge applied by the signal over the pulse duration is equal. In other embodiments, the pulses are monophasic pulses.

The pulses may be symmetric or asymmetric. A symmetric pulse is a pulse where the waveform when applying a positive charge to the nerve is symmetrical to the waveform when applying a negative charge to the nerve. An asymmetric pulse is a pulse where the waveform when applying a positive charge to the nerve is not symmetrical with the waveform when applying a negative charge to the nerve.

In an exemplary embodiment, the waveform is a pulse train with biphasic, asymmetric square pulses.

In some embodiments, the pulses are biphasic square pulses.

For embodiments of the signal comprising a pulse train, advantages have noted in respect of pulses of shorter pulse widths. Accordingly, in some embodiments, the duration of the pulses may be between 10 µs and 5 ms. For example, between 20 µs and 4 ms, between 50 µs and 2 ms, between 100 µs and 1 ms, or between 200 µs and 500 µs. These values include, in the case of a charge-balanced biphasic pulse, both positive and negative phases of the pulse.

Amplitude

For the purpose of the invention, the amplitude is referred to herein in terms of charge density per phase. Charge density per phase applied to the nerve by the electrical signal is defined as the integral of the current over one phase (e.g. over one phase of the biphasic pulse in the case of a charge-balanced biphasic pulse). Thus, charge density per phase applied to the nerve by the electrical signal is the charge per phase per unit of contact area between at least one electrode and the nerve, and also the integral of the current density over one phase of the signal waveform. Put another way, the charge density per phase applied to the nerve by the electrical signal is the charge per phase applied to the nerve by the electrical signal divided by the contact area between at least one electrode (generally the cathode) and the nerve.

The charge density per phase required by the invention represents the amount of energy required to stimulate neural activity in a nerve adjacent to the LGEA and/or a nerve adjacent to a SGA to increase immunosuppressive effects.

The inventors found the charge density per phase required to stimulate neural activity in a nerve adjacent to the LGEA and/or a nerve adjacent to a SGA to be between 5 µC to 150 µC per $cm^2$ per phase. For example, the charge density per phase applied by the electrical signal may be ≤10 µC per $cm^2$ per phase, ≤15 µC per $cm^2$ per phase, ≤20 µC per $cm^2$ per phase, ≤25 µC per $cm^2$ per phase, ≤30 µC per $cm^2$ per phase, ≤40 µC per $cm^2$ per phase, ≤50 µC per $cm^2$ per phase, ≤75 µC per $cm^2$ per phase, ≤100 µC per $cm^2$ per phase, ≤125 µC per $cm^2$ per phase, or ≤150 µC per $cm^2$ per phase. Additionally or alternatively, the charge density per phase applied by the electrical signal may be ≥5 µC per $cm^2$ per phase, ≥10 µC per $cm^2$ per phase, ≥15 µC per $cm^2$ per phase, ≥20 µC per $cm^2$ per phase, ≥25 µC per $cm^2$ per phase, ≥30 µC per $cm^2$ per phase, ≥40 µC per $cm^2$ per phase, ≥50 µC per $cm^2$ per phase, ≥75 µC per $cm^2$ per phase, ≥100 µC per $cm^2$ per phase, or ≥125 µC per $cm^2$ per phase.

Any combination of the upper and lower limits above is also possible.

The total charge applied to the nerve by the electrical signal in any given time period is a result of the charge density per phase of the signal, in addition to the frequency of the signal, the pattern of application of the signal and the area in contact between at least one electrode and the nerve. The frequency of the signal, the pattern of application of the signal and the area in contact between at least one electrode and the nerve are discussed further herein.

It will be appreciated by the skilled person that the amplitude of an applied electrical signal necessary to achieve the intended stimulation of the neural activity will depend upon the positioning of the electrode and the associated electrophysiological characteristics (e.g. impedance). It is within the ability of the skilled person to determine the appropriate current amplitude for achieving the intended modulation of the neural activity in a given subject.

It would be of course understood in the art that the electrical signal applied to the nerve would be within clinical safety margins (e.g. suitable for maintaining nerve signaling function, suitable for maintaining nerve integrity, and suitable for maintaining the safety of the subject). The electrical parameters within the clinical safety margin would typically be determined by pre-clinical studies.

In certain embodiments, where the neural interfacing element is suitable for placement on or around the nerve adjacent to the LGEA (and not the LGEA), or suitable for placement on or around the nerve adjacent to the SGA (and not the SGA), the amplitude may be at the lower end of the range discussed above.

It will be appreciated by the skilled person that the current amplitude of an applied electrical signal necessary to achieve the intended modulation of the neural activity will depend upon the positioning of the electrode and the associated electrophysiological characteristics (e.g. impedance). It is within the ability of the skilled person to determine the appropriate current amplitude for achieving the intended modulation of the neural activity in a given subject.

Episodic Application

Episodic application refers to where the electrical signal is applied to the nerve for a discrete number of episodes throughout a day. The electrical signal according to the invention may be applied for up to a maximum of six episodes per day. For example, the number of episodes of signal application per day may be one, two, three, four, five or six.

The electrical signal may be applied episodically every 2 to 3 hours. For example, the electrical signal may be applied episodically once every 2 hours, 2 hour 15 min, 2 hour 30 min, 2 hour 45 min, 3 hours.

Each episode may be defined by a set duration or a set number of iterations of the electrical signal. In some embodiments, each episode comprises applying to the nerve between 100 and 2400 pulses of the electrical signal, e.g. between 200 and 1200 pulses of the electrical signal, between 400 and 600 pulses of the electrical signal, etc. For example, each episode may comprise applying≤400, ≤800, ≤1200, ≤1600, ≤2000, or ≤2400 pulses of the electrical signal. In another example, each episode may comprise applying≤200, ≤400, ≤600, ≤800, ≤1000, or ≤1200 pulses of the electrical signal. In a further example, each episode may comprise applying≤400, ≤425, ≤450, ≤475, ≤500, ≤525, ≤550, ≤575, or ≤600 pulses of the electrical signal.

In other embodiments, each episode comprises between 20 and 40 iterations of the periodic pattern. For example, each episode comprises applying 20, 25, 30, 35, or 40 iterations of the periodic pattern, or any number therebetween. The higher the frequency, the lower the number of iterations.

As mentioned previously, in some embodiments, the episodes may be based on the subject's sleep-wake cycle, in particular the episodes may be whilst the subject is asleep. In some such embodiments, the episodes may be applied between 10 µm and 6 am. The sleep-wake cycle may be measured via known methods by detecting the subject's circadian rhythm phase markers (e.g. cortisol level, melatonin level or core body temperature), and/or a detector for detecting the subject's movements.

Periodic Application

Periodic application refers to where the electrical signal is applied to the nerve in a repeating pattern. The preferred repeating pattern is an on-off pattern, where the signal is applied for a first duration, referred to herein as an 'on' duration, then stopped for a second duration, referred to herein as an 'off' duration, then applied again for the first duration, then stopped again for the second duration, etc.

The periodic on-off pattern preferably has an on duration of between 0.1 and 10 s and an off duration of between 0.5 and 30 s. For example, the on duration may be ≤0.2 s, ≤0.5 s, ≤1 s, ≤2 s, ≤5 s, or ≤10 s. Alternatively or additionally, the on duration may be ≥0.1 s, ≥0.2 s, ≥0.5 s, ≥1 s, ≥2 s, or ≥5 s. Any combination of the upper and lower limits above for the on duration is also possible. For example, the off duration may be ≤1 s, ≤3 s, ≤5 s, ≤10 s, ≤15 s, ≤20 s, ≤25 s, or ≤30 s. Alternatively or additionally, the off duration may be ≥0.5 s, ≥1 s, ≥2 s, ≥5 s, ≥10 s, ≥15 s, ≥20 s, or ≤25 s. Any combination of the upper and lower limits above for the off duration is also possible.

In an exemplary embodiment, the periodic on-off pattern has an on duration of 0.5 s on, and 4.5 sec off.

Where the electrical signal is applied periodically and episodically, it means that the signal is applied in a periodic manner for each episode of application.

Periodic application may also be referred to as a duty cycled application. A duty cycle represents the percentage of time that the signal is applied to the nerve for a cycle of the periodic pattern. For example, a duty cycle of 20% may represent a periodic pattern having an on duration of 2 s, and an off duration of 10 s. Alternatively, a duty cycle of 20% may represent a periodic pattern having a on duration of 1 s, and an off duration of 5 s.

Duty cycles suitable for the present invention are between 0.1% and 100%.

Frequency

Frequency is defined as the reciprocal of the phase duration of the electrical waveform (i.e. 1/phase).

The inventors have found preferred frequencies for stimulating a nerve adjacent to the LGEA and/or a nerve adjacent to a SGA. In particular, the inventors have found preferred frequencies for embodiments where the electrical signal is applied periodically and for embodiments where the electrical signal is applied continuously.

In embodiments where the electrical signal is applied periodically, the electrical signal has a frequency of ≤300 Hz, preferably ≤50 Hz, more preferably ≤10 Hz. For example, the frequency of the electrical signal may be ≤50 Hz, ≤100 Hz, ≤150 Hz, ≤200 Hz, ≤250 Hz or ≤300 Hz. In other examples, the frequency of the electrical signal may be ≤10 Hz, ≤15 Hz, ≤20 Hz, ≤25 Hz, ≤30 Hz, ≤35 Hz, ≤40 Hz, ≤45 Hz, or ≤50 Hz. In further examples, the frequency may be ≤1 Hz, ≤2 Hz, ≤5 Hz, or ≤10 Hz. Additionally or alternatively, the frequency of the electrical signal may be ≥10 Hz, ≥15 Hz, ≥20 Hz, ≥25 Hz, ≥30 Hz, ≥35 Hz≥40 Hz, ≥45 Hz, or ≥50 Hz. In other examples, the frequency of the electrical signal may be ≥0.1 Hz, ≥0.2 Hz, ≥0.5 Hz, ≥1 Hz, ≥2 Hz, or ≥5 Hz. Any combination of the upper and lower limits above is also possible.

In embodiments where the electrical signal is applied continuously, the electrical signal has a frequency of ≤50 Hz, preferably ≤10 Hz, more preferably ≤2 Hz, even more preferably ≤1 Hz. For example, the frequency may be ≤1 Hz, ≤2 Hz, ≤5 Hz, or ≤10 Hz. In other examples the frequency may be ≤0.1 Hz, ≤0.2 Hz, ≤0.3 Hz, ≤0.4 Hz≤0.5 Hz, ≤0.6 Hz≤0.7 Hz, ≤0.8 Hz, or ≤0.9 Hz. Additionally or alternatively, the frequency of the electrical signal may be ≥0.1 Hz, ≥0.2 Hz, ≥0.5 Hz, ≥1 Hz, ≥2 Hz, or ≥5 Hz. Any combination of the upper and lower limits above is also possible.

In certain embodiments, the electrical signal has a frequency of 1 Hz to 50 Hz, for example 1 Hz to 30 Hz, 1 Hz to 20 Hz, 1 to 10 Hz, or 1 to 5 Hz. In some embodiments, the frequency is selected from any one of the group consisting of: ≤2 Hz, ≤5 Hz, ≤10 Hz, ≤15 Hz, ≤20 Hz, ≤25 Hz, ≤30 Hz, ≤35 Hz, ≤40 Hz, ≤45 Hz, or ≤50 Hz, though any frequency within the range may also be chosen. In other embodiments, the frequency is selected from any one of the group consisting of: ≥2 Hz, ≥5 Hz, ≥10 Hz, ≥15 Hz, or ≥20 Hz. Any combination of the upper and lower limits above is suitable with the invention.

The signal generator 117 may be configured to deliver one or more pulse trains at intervals according to the above-mentioned frequencies. For example, a frequency of 1 to 50 Hz results in a pulse interval between 1 pulse per second and 50 pulses per second, within a given pulse train.

Geometry of the Neural Interface/Neural Interfacing Elements

As explained above, the system comprises at least one neural interfacing element, preferably an electrode. In some embodiments, the at least one neural interfacing element is positioned on at least one neural interface. The at least one neural interface and/or neural interfacing element is configured to at least partially circumvent the nerve and may fully circumvent the nerve.

In some embodiments, the neural interface forms a cuff around the nerve (e.g. spiral cuff, helical cuff or flat interface). In other embodiments, the neural interface is a patch. In further embodiments, the neural interface is a clip comprising a first jaw pivoted at one end to a second jaw, and a biasing means (e.g. a mechanical spring) to bias the first and second jaw together.

The geometry of the at least one neural interface and/or neural interfacing element is defined in part by the anatomy of the nerve according to the invention. For example, the geometry of the neural interface and/or the at least one neural interfacing element may be limited by the length of the nerve and/or by the diameter of the nerve. The dimensions of the LGEA and SGAs, and their adjacent nerves, are shown in Tables 1 and 2 below.

In some embodiments, a nerve adjacent to the LGEA may be modulated by a neural interface and/or neural interfacing element that is suitable for placement on or around the nerve adjacent to the LGEA.

Preferably, the neural interface and/or neural interfacing element does not circumvent the LGEA. In these embodiments, the geometry of the neural interface and/or neural interfacing element may be determined by the diameter of the nerve adjacent to the LGEA (see Table 1). For instance, in embodiments where the neural interface and/or neural interfacing element at least partially circumvents the nerve adjacent to the LGEA, the surface of the neural interface and/or neural interfacing element facing the nerve defines an internal diameter, the size of which is determined by the diameter of the nerve adjacent to the LGEA. The neural interface and/or neural interfacing element may have an internal diameter of less than 500 μm, preferably less than 250 μm. Additionally, the internal diameter of the neural interface and/or neural interfacing element may be at least 10 μm, preferably at least 20 μm. For example, the neural interface and/or neural interfacing element may have a diameter of: ≥20 μm, ≥30 μm, ≥40 μm, ≥50 μm, ≥60 μm, ≥70 μm, ≥80 μm, ≥90 μm, ≥ 100 μm, ≥ 110 μm, ≥ 120 μm, ≥130 μm, ≥140 μm, ≥150 μm, ≥160 μm, ≥170 μm, ≥180 μm, ≥190 μm, ≥200 μm, ≥210 μm, ≥220 μm, ≥230 μm, ≥240 μm, or ≥250 μm. In other embodiments where the neural interface is a clip, the distance between the first and second jaw may extend at one end to at least any of the internal diameters specified above.

In some embodiments, a nerve adjacent to the LGEA may be modulated by a neural interface and/or neural interfacing element that is suitable for placement on or around both the nerve adjacent to the LGEA and the LGEA. In these embodiments, the geometry of the neural interface and/or neural interfacing element is determined by the diameter of the LGEA (see Table 1). For instance, in embodiments where the neural interface and/or neural interfacing element at least partially circumvents the nerve adjacent to the LGEA and the LGEA, the surface of the neural interface and/or neural interfacing element facing the nerve defines an internal diameter, the size of which is determined by the diameter of the nerve adjacent to the LGEA and the LGEA. The neural interface and/or neural interfacing element may have an internal diameter of less than 0.4 cm, preferably less than 0.25 cm.

Additionally, the internal diameter of the neural interface and/or neural interfacing element may be at least 0.02 cm, preferably at least 0.05 cm. For example, the neural interface and/or neural interfacing element may have an internal diameter of: ≥0.05 cm, ≥0.10 cm, ≥0.15 cm, ≥0.20 cm, or ≥0.25 cm.

In other embodiments where the neural interface is a clip, the distance between the first and second jaw may extend at one end to at least any of the internal diameters specified above.

In some embodiments, a nerve adjacent to a SGA is modulated by a neural interface and/or neural interfacing element that is suitable for placement on or around the nerve adjacent to the SGA.

Preferably, the neural interface and/or neural interfacing element does not circumvent the SGA. In these embodiments, the geometry of the neural interface and/or neural interfacing element may be determined by the diameter of the nerve adjacent to the SGA (see Table 1). For instance, in embodiments where the neural interface and/or neural interfacing element at least partially circumvents the nerve adjacent to the SGA, the surface of the neural interface and/or neural interfacing element facing the nerve defines an internal diameter, the size of which is determined by the diameter of the nerve adjacent to the SGA. The neural interface and/or neural interfacing element may have an internal diameter of less than 500 μm, preferably less than 300 μm. Additionally, the internal diameter of the neural interface and/or neural interfacing element may be at least 30 μm, preferably at least 50 μm. For example, the neural interface and/or neural interfacing element may have an internal diameter of: ≥50 μm, ≥100 μm, ≥150 μm, ≥200 μm, ≥250 μm, ≥300 μm, or ≥350 μm. In other embodiments where the neural interface is a clip, the distance between the first and second jaw may extend at one end to at least any of the internal diameters specified above.

In some embodiments, a nerve adjacent to a SGA may be modulated by a neural interface and/or neural interfacing element that is suitable for placement on or around both the nerve adjacent to the SGA and the SGA. In these embodiments, the geometry of the neural interface and/or neural interfacing element is determined by the diameter of the SGA (see Table 2). For instance, in embodiments where the neural interface and/or neural interfacing element at least partially circumvents the nerve adjacent to the LGEA and the LGEA, the surface of the neural interface and/or neural interfacing element facing the nerve defines an internal diameter, the size of which is determined by the diameter of the nerve adjacent to the SGA and the SGA. The neural interface and/or neural interfacing element may have an internal diameter of less than 0.5 cm, preferably less than 0.3 cm. Additionally, the internal diameter of the neural interface and/or neural interfacing element may be at least 0.02 cm, preferably at least 0.05 cm. For example, the neural interface and/or neural interfacing element may have an internal diameter of: ≥0.05 cm, ≥0.10 cm, ≥0.15 cm, ≥0.20 cm, ≥0.25 cm, ≥0.3 cm. In other embodiments where the neural interface is a clip, the distance between the first and second jaw may extend at one end to at least any of the internal diameters specified above.

In embodiments for modulating a nerve adjacent to a SGA and/or a nerve adjacent to the LGEA, the maximum length of the neural interface and/or the neural interfacing element may be defined by the length of the gastrosplenic ligament. The inventors found that the upper border of the gastrosplenic ligament in humans has an average length of 1.37 cm, with lengths ranging between 1.0 to 2.5 cm, whilst the lower border of the gastrosplenic ligament in humans has an average length of 6.50 cm, with lengths ranging between 2.5 to 13.0 cm. Accordingly, the neural interface and/or neural interfacing element may have a length of: ≤20 cm, ≤10 cm, ≤5 cm, ≤2 cm, ≤1 cm, ≤0.5 cm, ≤0.2 cm, or ≤0.1 cm.

There may be a plurality of neural interfaces, each neural interface with at least one neural interfacing element to define multiple sites for applying a signal. In some embodiments, the multiple sites may be located along a single nerve, either along the nerve adjacent to the LGEA or along the nerve adjacent to a SGA. For example, a first neural interface may define a first site on the nerve adjacent to the LGEA which is proximal to the spleen, and a second neural interface may define a second site on the nerve adjacent to the LGEA which is distal to the spleen. In other embodiments, the multiple sites may be located on more than one nerve, for example on the nerve adjacent to the LGEA and the nerve adjacent a SGA, or on the nerves adjacent to more than one SGA. Multiple sites along more than one nerve is useful with the invention.

Neural Interfacing Elements

When applying an electrical signal, the neural interfacing element is preferably an electrode.

Electrode types suitable for the present invention are known in the art. For example, [20] disclose several types of electrode for non-damaging neural tissue modulation. The document discloses cuff electrodes (e.g. spiral cuff, helical cuff or flat interface), and flat interface electrodes, both of which are also suitable for use with the present invention. A mesh, a linear rod-shaped lead, paddle-style lead or disc contact electrode (including multi-disc contact electrodes) are also disclosed in [20] and would be suitable for use in the present invention. A hook electrode, such as a hook electrode from Harvard Apparatus (Holliston, USA), is useful for acute electrical stimulation. A bipolar electrode, such as a bipolar electrode from Cortec (Freiburg, Germany), is useful for chronic implantation. A sling electrode also suitable for the present invention. Also suitable for the present invention are intrafascicular electrode, glass suction electrode, paddle electrode, bipolar hemi-cuff electrode, bipolar hook electrode, percutaneous cylindrical electrode.

Electrodes may be monopolar, bipolar, tripolar, quadripolar or have five or more poles. The electrodes may fabricated from, or be partially or entirely coated with, a high charge capacity material such as platinum black, iridium oxide, titanium nitride, tantalum, poly(elthylenedioxythiophene) and suitable combinations thereof.

In some embodiments, a plurality of electrodes may be positioned at a single site for applying a signal.

For example, there may be two or three electrodes for applying a signal. In such embodiments, the electrodes may be positioned on a neural interface such that, in use, the electrodes are located transversely along the axis of the nerve. The surface area of the electrode which is in contact with the nerve is may be approximately equal for each electrode. Alternatively or additionally, the electrodes may be positioned at different locations around the circumference of the LGEA and/or SGA, each electrode positioned to selectively stimulate a particular nerve or bundle of nerves adjacent to the LGEA and/or SGA.

The plurality of electrodes at a single site may be insulated from one another by a non-conductive biocompatible material. To this end, the neural interface 108 may comprise a non-conductive biocompatible material which is spaced transversely along the nerve when the device is in use.

In some embodiments, each of the plurality of electrodes may be individually electrically excitable. In these embodiments, the signal generator is electrically connected to each electrode separately via one of a plurality of electrical leads, or by any other method known in the art. The signal generator, or a plurality of signal generators, may then apply a different electrical signal to each of the plurality of electrodes. In some instances, no electrical signal may be applied to some of the plurality of electrodes.

For example, a plurality of electrodes may be positioned at different locations around the circumference of the LGEA, where each electrode is individually excitable. In this example, the signal generator may apply an electrical signal to at least one electrode which is positioned on a selected nerve adjacent the LGEA. Thus, only neural activity in the selected nerve adjacent the LGEA would be stimulated. In other words, the nerve is selectively stimulated.

Reference [20] discloses separated-interface nerve electrodes, and in particular forms of ionic coupling electrodes (for example in the form of a cuff electrode) that facilitates the application of a prolonged single phase current to a nerve which mitigates the kind of nerve damage described elsewhere herein.

This kind of electrode would be suitable for use in the present invention.

In some embodiments (for example, FIG. 2), at least one electrode 109 may be coupled to implantable device 106 of system 116 via electrical leads 107. Alternatively, implantable device 106 may be directly integrated with the at least one electrode 109 without leads. In any case, implantable device 106 may comprise DC current blocking output circuits, optionally based on capacitors and/or inductors, on all output channels (e.g. outputs to the at least one electrode 109, or physiological sensor 111).

An advantage of the present invention is that the development of the neural interface and/or neural interfacing element for a nerve adjacent to the LGEA and/or a nerve adjacent to a SGA is easier compared to development for the nerves adjacent to the splenic arterial artery. This is because pulsation of the LGEA and the SGAs are minimal compared to the SA.

Other Suitable Forms of Neural Interfacing Element and Signal

The signal may comprise an electromagnetic signal, such as an optical signal. Optical signals can conveniently be applied using a laser and/or a light emitting diode configured to apply the optical signal. Optogenetics is a technique in which genetically-modified cells express photosensitive features, which can then be activated with light to modulate cell function. Many different optogenetic tools have been developed for stimulating neural firing. A list of optogenetic tools to suppress neural activity is compiled in [21]. Thus light can be used with genetic modification of target cells to achieve stimulation of neural activity.

The signal may use thermal energy, and the temperature of a nerve can be modified to stimulate the propagation of neural activity. Heating the nerve can be used to modulate neural activity. In certain such embodiments, the neural interface is a small implantable or wearable neural interfacing element or device for radiant electromagnetic heating using visible, infrared, or microwave radiation, for example using a laser diode or a light emitting diode. In certain alternative embodiments, the neural interface is a small implantable or wearable neural interfacing element or device for conductive heating, such as an electrically resistive element, which can be used to provide a fast, reversible, and spatially very localized heating effect (see for example [21]).

The signal may comprise a mechanical signal. In certain embodiments, the mechanical signal is a pressure signal. In certain such embodiments, the neural interface is a neural interfacing element which generates pressure to be applied to the nerve which stimulates neural activity.

Another mechanical form of signal is an ultrasonic signal. In certain embodiments, the neural interface is an ultrasound neural interfacing element for modulating neural activity uses ultrasound which may conveniently be implemented using external, for example wearable, instead of implanted, ultrasound neural interfacing elements.

Microprocessor

The system 116, in particular the implantable device 106, may comprise a processor, for example microprocessor 113. Microprocessor 113 may be responsible for triggering the beginning and/or end of the signals delivered to the nerve by the at least one neural interfacing element. Optionally, microprocessor 113 may also be responsible for generating and/or controlling the signal parameters.

Microprocessor 113 may be configured to operate in an open-loop fashion, wherein a pre-defined signal (e.g. as described above) is delivered to the nerve at a given periodicity (or continuously) and for a given duration (or indefinitely) with or without an external trigger, and without any control or feedback mechanism. Alternatively, microprocessor 113 may be configured to operate in a closed-loop fashion, wherein a signal is applied based on a control or feedback mechanism. As described elsewhere herein, the external trigger may be an external controller 101 operable by the operator to initiate delivery of a signal.

Microprocessor 113 of the system 116, in particular of the implantable device 106, is preferably constructed so as to generate, in use, a preconfigured and/or operator-selectable signal that is independent of any input. In other embodiments, microprocessor 113 is responsive to an external signal, more preferably information (e.g. data) pertaining to one or more physiological parameters of the subject.

Microprocessor 113 may be triggered upon receipt of a signal generated by an operator, such as a physician or the subject in which the device 106 is implanted. To that end, the system 116 may be part of a system 100 which additionally comprises an external system 118 comprising a controller 101. An example of such a system is described below with reference to FIG. 2.

External system 118 of wider system 100 is external to the system 116 and external to the subject, and comprises controller 101. Controller 101 may be used for controlling and/or externally powering system 116. To this end, controller 101 may comprise a powering unit 102 and/or a programming unit 103. The external system 118 may further comprise a power transmission antenna 104 and a data transmission antenna 105, as further described below.

The controller 101 and/or microprocessor 113 may be configured to apply any one or more of the above signals to the nerve periodically or continuously, and/or episodically. Hence, the signal may be applied: (i) continuously, (ii) periodically, (iii) episodically, (iv) continuously and episodically, or (iv) periodically and episodically.

Episodic application refers to where the electrical signal is applied to the nerve for a discrete number of episodes throughout a day. In some embodiments, the signal is preferably applied for a maximum of 6 episodes per day.

Each episode may be defined by a certain duration and/or a certain number of iterations of the electrical signal.

In some embodiments, e.g. where a high frequency signal such as >5 Hz is used, the preferred duration of an episode for application of the signal to the nerve is less than 10 min, and more preferably between 2 and 5 min. For example, the signal may be applied for one of: ≤2 min 30 sec, ≤3 min, ≤30 min 30 sec, ≤4 min, ≤4 min 30 sec, or ≤5 min. Alternatively or additionally, the signal may be applied for one of: ≥2 min, ≥2 min 30 sec, ≥3 min, ≥30 min 30 sec, ≥4 min, or ≥4 min 30 sec.

In other embodiments, e.g. where a low frequency signal such as ≤5 Hz is used, the preferred duration of an episode for application of the signal to the nerve is less than 2 hours. For example, the signal may be applied for one of: ≤30 min, ≤45 min, ≤1 hour, ≤1 hour 15 min, ≤1 hour 30 min, ≤1 hour 45 min, or ≤2 hours. Alternatively or additionally, the signal may be applied for one of: ≥15 min, ≥30 min, ≥45 min, ≥1 hour, ≥1 hour 15 min, ≥1 hour 30 min, or ≥1 hour 45 min.

The duration of an episode for application of the signal to the nerve may additionally or alternatively be defined by the total number of pulses applied to the nerve. Preferably between 120 and 3000 pulses are applied to the nerve per episode.

Continuous application refers to where the electrical signal is applied to the nerve in a continuous manner. Where the electrical signal is applied continuously and episodically, it means that the signal is applied in a continuous manner for each episode of application. In embodiments where the electrical signal is a series of pulses, the gaps between those pulses (i.e. between the pulse width and the phase duration) do not mean the signal is not continuously applied.

Continuous application may continue indefinitely, e.g. permanently. Alternatively, the continuous application may be for a minimum period, for example the signal may be continuously applied for at least 5 days, or at least 7 days.

Periodic application refers to where the electrical signal is applied to the nerve in a repeating pattern (e.g. an on-off pattern). Where the electrical signal is applied periodically and episodically, it means that the signal is applied in a periodic manner for each episode of application.

The preferred repeating pattern is an on-off pattern, where the signal is applied is applied for a first duration, referred to herein as an 'on' duration, then stopped for a second duration, referred to herein as an 'off' duration, then applied again for the first duration, then stopped again for the second duration, etc. This type of periodic signal application is sometimes referred to as burst signal application.

The periodic on-off pattern may have an 'on' duration of between 0.1 and 10 s and an 'off' duration of between 2 and 30 s. For example, the 'on' duration may be ≤0.2 s, ≤0.5 s, ≤1 s, ≤2 s, ≤5 s, or ≤10 s. For example, the 'off' duration may be ≤5 s, ≤10 s, ≤15 s, ≤20 s, ≤25 s, or ≤30 s. For signals with high frequencies (e.g. 30 Hz), the 'on' duration is preferably towards the lower limit of the range (e.g. 0.1 s) and the 'off' duration is preferably toward the upper limit of the range (e.g. 30 s). As the frequency decreases, the 'on' duration may increase, and the 'off' duration may decrease.

In certain embodiments, the signal is applied only when the subject is in a specific state e.g. only when the subject is awake, only when the subject is asleep, prior to and/or after the ingestion of food, prior to and/or after the subject undertakes exercise, etc.

The various embodiments for timing for modulation of neural activity in the nerve can all be achieved using controller 101 in a system of the invention.

Other components of the system including the implantable device In addition to the aforementioned at least one neural interfacing element (e.g. electrode 109) and microprocessor 113, the system 116 may comprise one or more of the following components: implantable transceiver 110; physiological sensor 111; power source 112; memory 114 (otherwise referred to as a non-transitory computer-readable storage device); and physiological data processing module 115. Additionally or alternatively, the physiological sensor 111; memory 114; and physiological data processing module 115 may be part of a sub-system external to the system.

Optionally, the external sub-system may be capable of communicating with the system, for example wirelessly via the implantable transceiver 110.

In some embodiments, one or more of the following components may be contained in the implantable device 106: power source 112; memory 114; and a physiological data processing module 115.

The power source 112 may comprise a current source and/or a voltage source for providing the power for the signal delivered to a nerve adjacent to the LGEA and/or a nerve adjacent to a SGA by the at least one neural interfacing element (e.g. electrode 109). The power source 112 may also provide power for the other components of the implantable device 106 and/or system 116, such as the microprocessor 113, memory 114, and implantable transceiver 110. The power source 112 may comprise a battery, the battery may be rechargeable.

It will be appreciated that the availability of power is limited in implantable devices, and the invention has been devised with this constraint in mind. The implantable device 106 and/or system 116 may be powered by inductive powering or a rechargeable power source.

Memory 114 may store power data and data pertaining to the one or more physiological parameters from internal system 116. For instance, memory 114 may store data pertaining to one or more signals indicative of the one or more physiological parameters detected by physiological sensor 111, and/or the one or more corresponding physiological parameters determined via physiological data processing module 115. In addition or alternatively, memory 114 may store power data and data pertaining to the one or more physiological parameters from external system 118 via the implantable transceiver 110.

To this end, the implantable transceiver 110 may form part of a communication subsystem of the wider system 100, as is further discussed below.

Physiological data processing module 115 is configured to process one or more signals indicative of one or more physiological parameters detected by the physiological sensor 111, to determine one or more corresponding physiological parameters. Physiological data processing module 115 may be configured for reducing the size of the data pertaining to the one or more physiological parameters for storing in memory 114 and/or for transmitting to the external system via implantable transceiver 110.

Implantable transceiver 110 may comprise one or more antenna(e). The implantable transceiver 100 may use any suitable signaling process such as RF, wireless, infrared and so on, for transmitting signals outside of the body, for instance to wider system 100 of which the system 116 is one part.

Alternatively or additionally, physiological data processing module 115 may be configured to process the signals indicative of the one or more physiological parameters and/or process the determined one or more physiological parameters to determine the evolution of the disease in the subject. In such case, the system 116, in particular the implantable device 106, will include a capability of calibrating and tuning the signal parameters based on the one or more physiological parameters of the subject and the determined evolution of the disease in the subject.

The physiological data processing module 115 and the at least one physiological sensor 111 may form a physiological sensor subsystem, also known herein as a detector, either as part of the system 116, part of the implantable device 106, or external to the system.

Physiological sensor 111 comprises one or more sensors, each configured to detect a signal indicative of one of the one or more physiological parameters described above. For example, the physiological sensor 110 is configured for: detecting biomolecule concentration using electrical, RF or optical (visible, infrared) biochemical sensors; detecting blood flow using intra- or perivascular flow tubes in or around the artery; detecting blood pressure using an invasive blood pressure monitor comprising a cannula in the artery; detecting neural activity of a nerve using an electrical sensor; or a combination thereof. As previously mentioned, detecting splenic blood flow and systolic pressure are particularly useful in the present invention.

In other examples, the detector may be configured for detecting the subject's movement using an accelerometer. The accelerometer determines when the subject is asleep by determining if the subject is lying down, i.e. if there has been an extended period (e.g. >70 min) in which the subject has maintained a substantially lying down position. This determination is based on the orientation and acceleration of experienced and measured by the accelerometer.

The physiological parameters determined by the physiological data processing module 115 may be used to trigger the microprocessor 113 to deliver a signal of the kinds described above to the nerve using the at least one neural interfacing element (e.g. electrode 109). Upon receipt of the signal indicative of a physiological parameter received from physiological sensor 111, the physiological data processor 115 may determine the physiological parameter of the subject, and the evolution of the disease, by calculating in accordance with techniques known in the art. For instance, if a signal indicative of excessive TNF concentration in the circulation is detected, the processor may trigger delivery of a signal which dampens secretion of the respective signaling molecule, as described elsewhere herein.

The memory 114 may store physiological data pertaining to normal levels of the one or more physiological parameters. The data may be specific to the subject into which the system 116 is implanted, and gleaned from various tests known in the art. Upon receipt of the signal indicative of a physiological parameter received from physiological sensor 111, or else periodically or upon demand from physiological sensor 111, the physiological data processor 115 may compare the physiological parameter determined from the signal received from physiological sensor 111 with the data pertaining to a normal level of the physiological parameter stored in the memory 114, and determine whether the received signals are indicative of insufficient or excessive of a particular physiological parameter, and thus indicative of the evolution of the disease in the subject.

The system 116 and/or implantable device 106 may be configured such that if and when an insufficient or excessive level of a physiological parameter is determined by physiological data processor 115, the physiological data processor 115 triggers delivery of a signal to the nerve by the at least one neural interfacing element (e.g. electrode 109), in the manner described elsewhere herein. For instance, if physiological parameter indicative of worsening of any of the physiological parameters and/or of the disease is determined, the physiological data processor 115 may trigger delivery of a signal which dampens secretion of the respective biochemical, as described elsewhere herein. Particular physiological parameters relevant to the present invention are described above. When one or more signals indicative of one or more of these physiological parameters are received by the physiological data processor 115, a signal may be applied to the nerve via the at least one neural interfacing element (e.g. electrode 109).

In some embodiments, controller 101 may be configured to make adjustments to the operation of the system 116. For instance, it may transmit, via a communication subsystems (discussed further below), physiological parameter data pertaining to a normal level of signaling molecules secreted from the spleen. The data may be specific to the patient into which the device is implanted. The controller 101 may also be configured to make adjustments to the operation of the power source 112, signal generator 117 and processing elements 113, 115 and/or neural interfacing elements in order to tune the signal delivered to the nerve by the neural interface.

As an alternative to, or in addition to, the ability of the system 116 and/or implantable device 106 to respond to physiological parameters of the subject, the microprocessor 113 may be triggered upon receipt of a signal generated by an operator (e.g. a physician or the subject in which the system 116 is implanted). To that end, the system 116 may be part of a wider system 100 which comprises external system 118 and controller 101, as is further described below.

System Including Implantable Device

With reference to FIG. 2, the implantable device 106 of the invention may be part of a wider system 100 that includes a number of subsystems, for example the system 116 and the external system 118.

The external system 118 may be used for powering and programming the system 116 and/or the implantable device 106 through human skin and underlying tissues.

The external subsystem 118 may comprise, in addition to controller 101, one or more of: a powering unit 102, for wirelessly recharging the battery of power source 112 used to power the implantable device 106; and, a programming unit 103 configured to communicate with the implantable transceiver 110. The programming unit 103 and the implantable transceiver 110 may form a communication subsystem. In some embodiments, powering unit 102 is housed together with programming unit 103. In other embodiments, they can be housed in separate devices.

The external subsystem 118 may also comprise one or more of: power transmission antenna 104; and data transmission antenna 105. Power transmission antenna 104 may be configured for transmitting an electromagnetic field at a low frequency (e.g., from 30 kHz to 10 MHz). Data transmission antenna 105 may be configured to transmit data for programming or reprogramming the implantable device 106, and may be used in addition to the power transmission antenna 104 for transmitting an electromagnetic field at a high frequency (e.g., from 1 MHz to 10 GHz). The temperature in the skin will not increase by more than 2 degrees Celsius above the surrounding tissue during the operation of the power transmission antenna 104. The at least one antennae of the implantable transceiver 110 may be configured to receive power from the external electromagnetic field generated by power transmission antenna 104, which may be used to charge the rechargeable battery of power source 112.

The power transmission antenna 104, data transmission antenna 105, and the at least one antennae of implantable transceiver 110 have certain characteristics such a resonant frequency and a quality factor (Q). One implementation of the antenna(e) is a coil of wire with or without a ferrite core forming an inductor with a defined inductance. This inductor may be coupled with a resonating capacitor and a resistive loss to form the resonant circuit. The frequency is set to match that of the electromagnetic field generated by the power transmission antenna 105. A second antenna of the at least one antennae of implantable transceiver 110 can be used in system 116 for data reception and transmission from/to the external system 118. If more than one antenna is used in the system 116, these antennae are rotated 30 degrees from one another to achieve a better degree of power transfer efficiency during slight misalignment with the with power transmission antenna 104.

External system 118 may comprise one or more external body-worn physiological sensors 121 (not shown) to detect signals indicative of one or more physiological parameters. The signals may be transmitted to the system 116 via the at least one antennae of implantable transceiver 110. Alternatively or additionally, the signals may be transmitted to the external system 116 and then to the system 116 via the at least one antennae of implantable transceiver 110. As with signals indicative of one or more physiological parameters detected by the implanted physiological sensor 111, the signals indicative of one or more physiological parameters detected by the external sensor 121 may be processed by the physiological data processing module 115 to determine the one or more physiological parameters and/or stored in memory 114 to operate the system 116 in a closed-loop fashion. The physiological parameters of the subject determined via signals received from the external sensor 121 may be used in addition to alternatively to the physiological parameters determined via signals received from the implanted physiological sensor 111.

For example, in a particular embodiment a detector external to the implantable device may include a non-invasive blood flow monitor, such as an ultrasonic flowmeter and/or a non-invasive blood pressure monitor, and determining changes in physiological parameters, in particular the physiological parameters described above. As explained above, in response to the determination of one or more of these physiological parameters, the detector may trigger delivery of signal to a nerve adjacent to the LGEA and/or a nerve adjacent to a SGA by the at least one neural interfacing element (e.g. electrode 109), or may modify the parameters of the signal being delivered or a signal to be delivered to the nerve by the at least one neural interfacing element in the future.

The wider system 100 may include a safety protection feature that discontinues the electrical stimulation of the nerve in the following exemplary events: abnormal operation of the system 116 (e.g. overvoltage); abnormal readout from an implanted physiological sensor 111 (e.g. temperature increase of more than 2 degrees Celsius or excessively high or low electrical impedance at the electrode-tissue interface); abnormal readout from an external body-worn physiological sensor 121 (not shown); or abnormal response to stimulation detected by an operator (e.g. a physician or the subject). The safety precaution feature may be implemented via controller 101 and communicated to the system 116, or internally within the system 116.

The external system 118 may comprise an actuator 120 (not shown) which, upon being pressed by an operator (e.g. a physician or the subject), will deliver a signal, via controller 101 and the respective communication subsystem, to trigger the microprocessor 113 of the system 116 to deliver a signal to the nerve by the at least one neural interfacing element (e.g. electrode 109).

Wider system 100 of the invention, including the external system 118, but in particular system 116, is preferably made from, or coated with, a biostable and biocompatible material. This means that the system is both protected from damage due to exposure to the body's tissues and also minimizes the risk that the system elicits an unfavorable reaction by the host (which could ultimately lead to rejection). The material used to make or coat the system should ideally resist the formation of biofilms. Suitable materials include, but are not limited to, poly(3,4-ethylenedioxythiophene):p-toluenesulfonate (PEDOT:PTS or PEDT), poly(p-xylylene) polymers (known as Parylenes) and polytetrafluoroethylene.

The implantable device 116 of the invention will generally weigh less than 50 g.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless otherwise indicated each embodiment as described herein may be combined with another embodiment as described herein.

BRIEF DESCRIPTION OF THE DRAWINGS

FIG. 7 is a histological image of the SGAs and nerves in Yucatan pigs.

FIG. 11 shows the percent change in splenic artery blood flow and mean arterial blood pressure (mean BP) during stimulation (10 Hz, 400 us/phase, biphasic, 12 mA for 1 minute) delivered through a cuff on the gastroepiploic nerve (GE) prior to (panel GE Stimulation) and after GE nerve transection (panel GE-X Transection+Stimulation). Prior to transection of the GE nerve stimulation for 1 minute (represented by the line with 12 mA) decreased splenic artery blood flow measured using a transit time flow probe placed on the splenic artery along the hilum of the spleen by approximately 15%. Mean BP did not change during stimulation. After ligating and cutting the GE both afferently and efferently the same stimulation parameters splenic artery blood flow was abolished (panel GE-X).

MODES FOR CARRYING OUT THE INVENTION

Figure 1A:
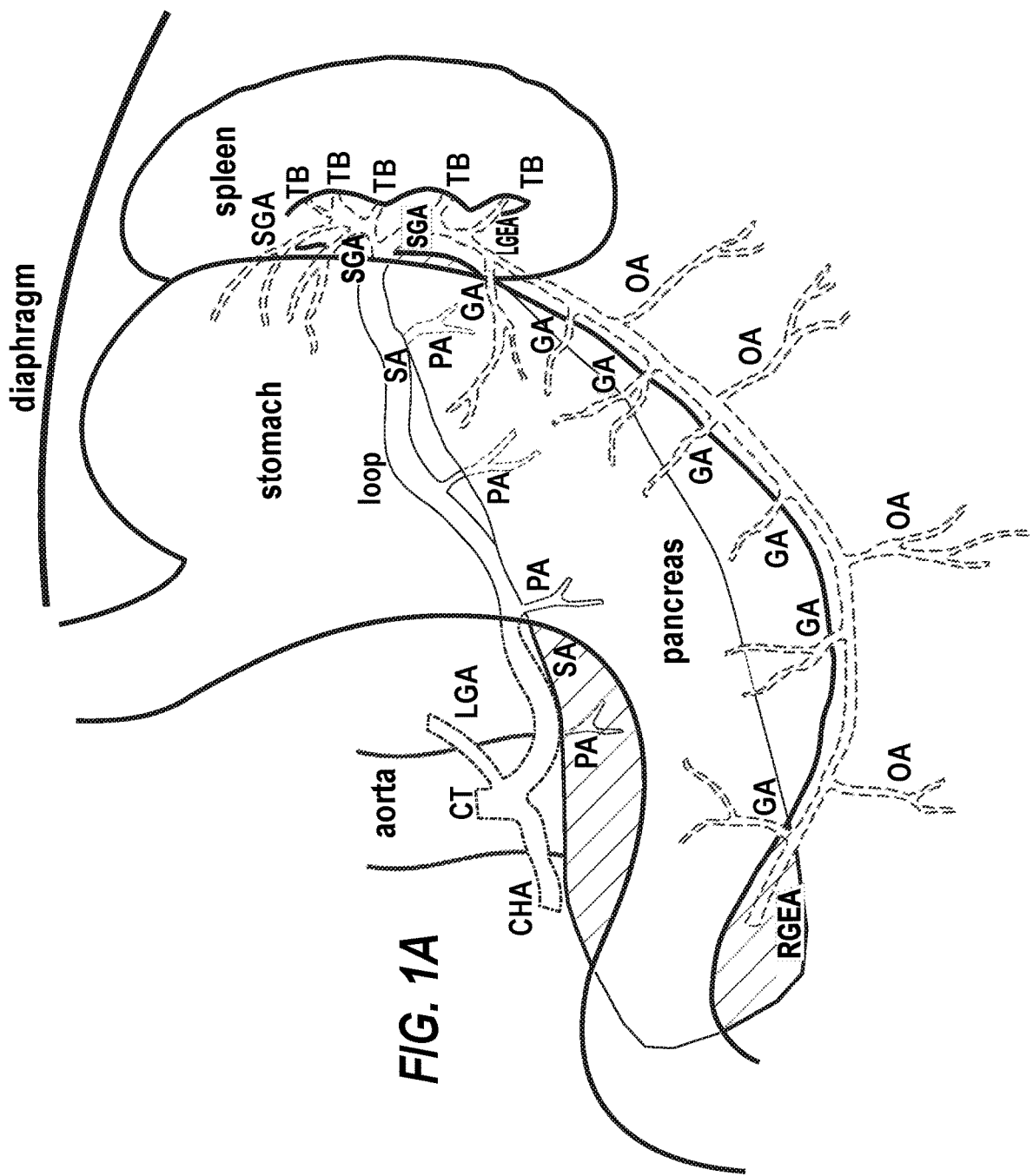
FIG. 1A is a ventral view of splenic vascularization in relation to the stomach and pancreas, where "CT" is the coeliac trunk, "GA" is the gastric artery, "LGEA" is the left gastroepiploic artery, "OA" is the omental artery, "PA" is pancreatic artery, "SA" is splenic artery, "RGEA" is right gastroepiploic artery, "SGA" is short gastric artery, and "TB" is terminal branch. Dash-dotted line outlines the blood vessels.
Figure 1B:
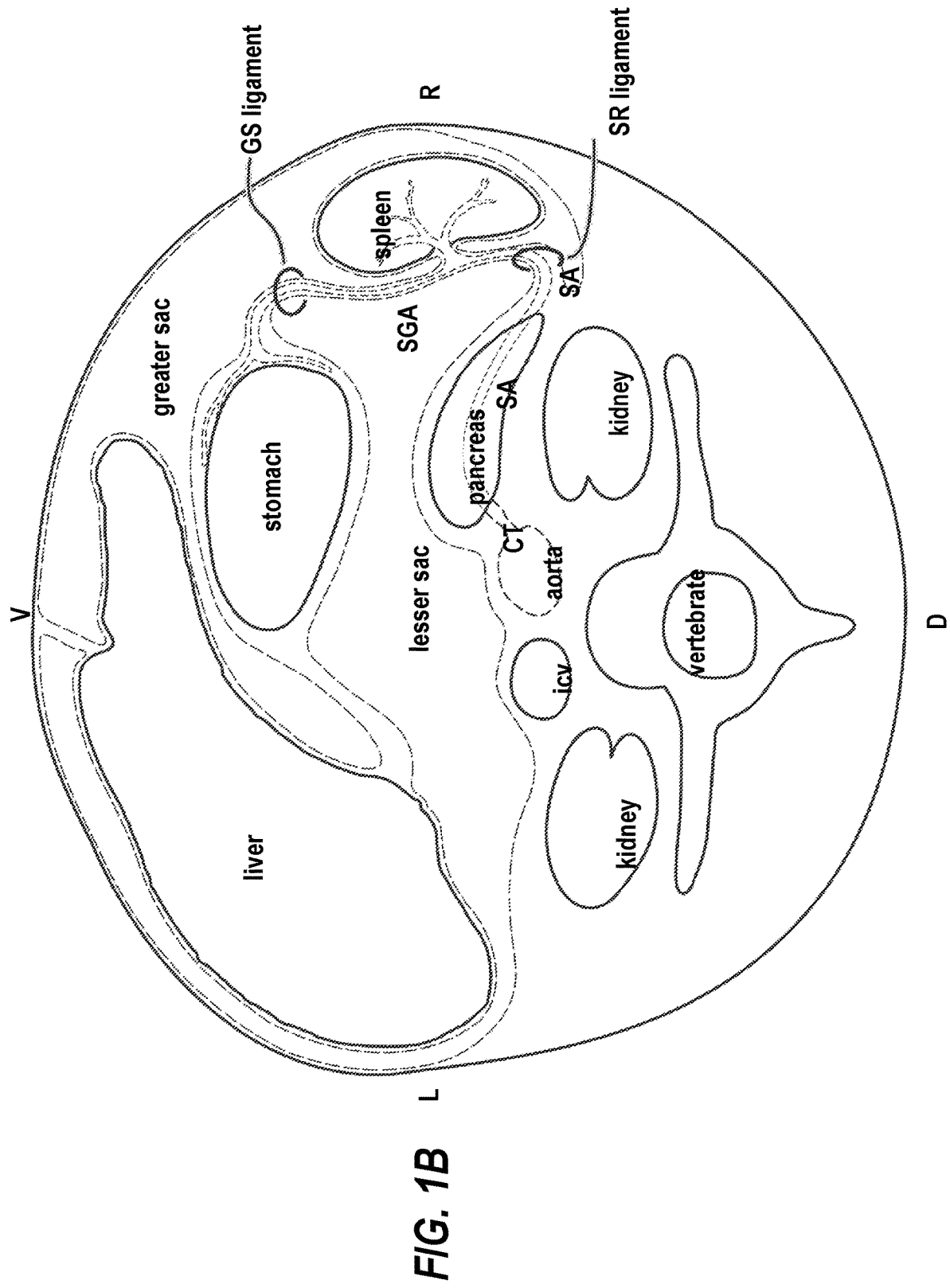
FIG. 1B is a transversal section through the upper abdomen illustrating the course of the splenic artery and a short gastric artery, where "GS ligament" is gastrosplenic ligament, "SGA" is short gastric artery, "SR ligament" is splenorenal ligament, "SA" is splenic artery, "V" is ventral, "D" is dorsal, "L" is left, and "R" is right. Dashed line outlines the peritoneum. Dash-dotted line outlines blood vessels.
Figure 2:
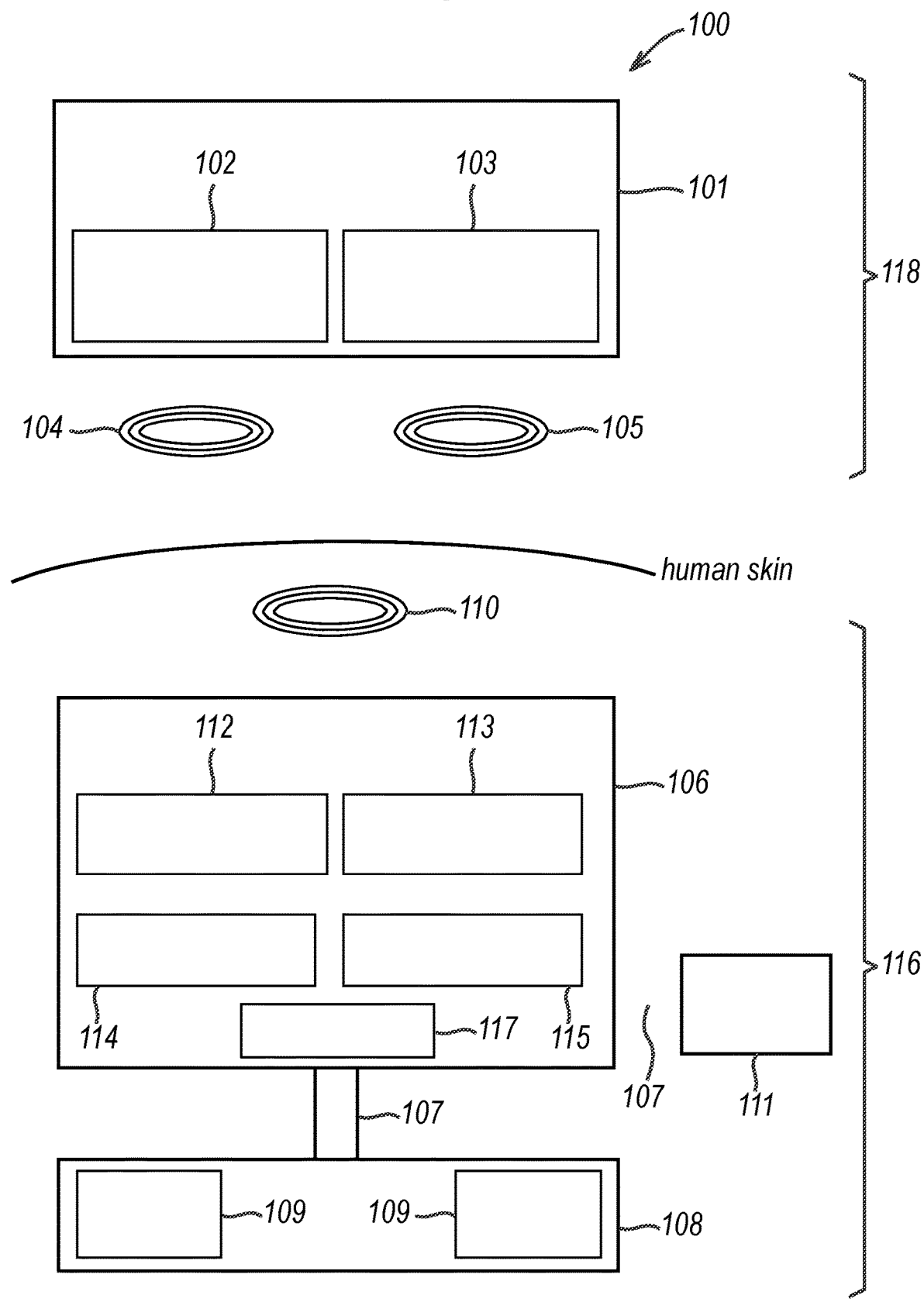
FIG. 2 is a block diagram illustrating elements of a system for performing electrical modulation in the nerve according to the present invention.

Study 1: Neurovascular Structures Going to the Spleen

The neurovascular structures going to the spleen in humans were investigated. In particular, next to the main splenic artery (SA) and nerve plexus, the area around the gastro splenic ligament, including the SGAs and the LGEA, were analyzed.

Six formaldehyde preserved cadavers were studied. The donors gave informed consent for the use of their tissues. Tissue blocks of the spleen, stomach, pancreas, greater omentum, gastrosplenic ligament and if present the phrenic splenic ligament were removed as a whole. The tissues were dissected and then tissue samples of the SA and its branches and of both ligaments were isolated and processed for histology. Different immunohistochemical stainings for nervous tissue were performed on adjacent slides, by means of antibodies raised against Protein Gene Product 9.5 (PGP9.5), Tyrosine Hydroxylase (TH) and Calcitonin Gene-Related Peptide (CGRP), respectively staining general, sympathetic and afferent nervous tissue. A specific substrate to visualize the bound antibodies was used to perform both brightfield and fluorescent microscopy on the same samples.

Materials and Methods

Collection of Material; Macroscopic Dissection

Tissue blocks of six cadavers that were embalmed by arterial perfusion with 4% formaldehyde were collected including the spleen, stomach, pancreas, greater omentum, gastrosplenic ligament and if present the phrenic splenic ligament.

Dissection

Dissection was performed mostly macroscopically and occasionally with a surgical microscope. During the dissection a photographic log was kept.

Histology

After extraction of all descriptive and quantitative dissection parameter data, samples of the gastrosplenic ligament, the phrenic splenic ligament and several places of the SA and its branches were removed for histological examination. All samples were degreased in 100% acetone for one hour and arterial samples were treated with a decalcifying agent (12.5% EDTA in distilled water, pH 7.5) for six days. After these pretreatments, all samples were further processed for paraffin embedding and sequentially placed in increasing percentages of ethanol, xylene and finally liquid paraffin. Sample blocks were cut on a microtome and 5 μm thick slices were alternately placed on glass slides. Subsequently, the sample slices were stretched and dried by placing the glass slides on a 60° C. plate for two hours.

Adjacent slides of each sample were stained with a PGP9.5, a TH, and a CGRP staining. First, the samples were deparaffinated by placing tissue slides sequentially in xylene, decreasing percentages of ethanol and distilled water, after which the slides were incubated with citrate buffer (room temperature) for five minutes. Next, the slides were placed in citrate buffer with a temperature of 95° C. for antigen retrieval (20 minutes). After cooling down and several washing steps with distilled water and Tris-buffered saline (TBS)+tween, tissue slides were pre-incubated with 5% Normal Human Serum in TBS-buffer for ten minutes, followed by incubation with primary antibodies (Rabbit anti-PGP (DAKO) (1:2000) 48 hours (40 C), rabbit anti-TH (PelFreez) (1:1500) overnight (RT) or mouse anti-CGRP (Sigma) (1:1500) overnight (40 C)) in TBS-buffer+3% BSA. Thereafter, tissue slides were washed with TBS-buffer+tween several times and incubated for 30 minutes with Brightvision Poly-AP Goat-anti-Rabbit (ImmunoLogic) (PGP and TH) or Brightvision Poly-AP Goat-anti-Mouse (ImmunoLogic) (CGRP). After washing with TBS-buffer several times, the samples were incubated with Liquid Permanent Red (LPR) (DAKO) for ten minutes, resulting in a pinkish precipitation reaction at the side of the antibodies-tissue complex. The slides were washed with distilled water and dipped in hematoxylin for counterstaining. Finally, the slides were placed in flowing tap water and rinsed in distilled water one last time after which they were placed in the 600 C stove for 90 minutes.

Subsequently, the slides were enclosed with entellan (diluted with xylene) and coverslipped. In addition, for each marker a negative control without the primary antibody was included. Samples of the vagus nerve were included as a positive control for afferent nervous tissue (CGRP staining). Intrinsic vessel wall innervation was used as a positive control for general and sympathetic nervous tissue (resp. PGP and TH staining).

Image Analysis

Both brightfield and fluorescent single images and tile scans were captured using a Leica DM6 microscope with a motorized scanning stage, a Leica DFC7000 T camera and Leica LASX software.

For fluorescent images of the LPR substrate, the 13 fluorescent filter (band pass excitation at 450-490 nm and long pass suppression at 515 nm) of Leica was used. The image quality was set to 8-bit and the image format to Bin 2×2. The settings for the brightfield images were; intensity: 255, aperture: 27, field diaphragm: 33, exposure: 3.73 ms, gain: 1.0. The settings for the fluorescent images were; FIM: 100%, Il-Fld: 6, exposure: 300 ms, gain: 1.1. Of each artery sample with surrounding nerve bundles, tile scans were made using the microscope. Multiple images were captured with a 20× magnification and automatically stitched to make a tile scan. Tile scans were made with a 20× magnification and were saved as jpg files. Tile scans of TH stained samples were analyzed using FIJI (ImageJ with additional plugins) and several parameters were extracted according to a pre-defined image analysis protocol. Nerve bundles with an area less than 400 μm2 were excluded, since this is most likely representing nervous tissue supplying the vessel wall itself (van Amsterdam et al, 2016).

Results

Left Gastric Epiploic Artery (LGEA) and the Adjacent Nerves

Figure 3:
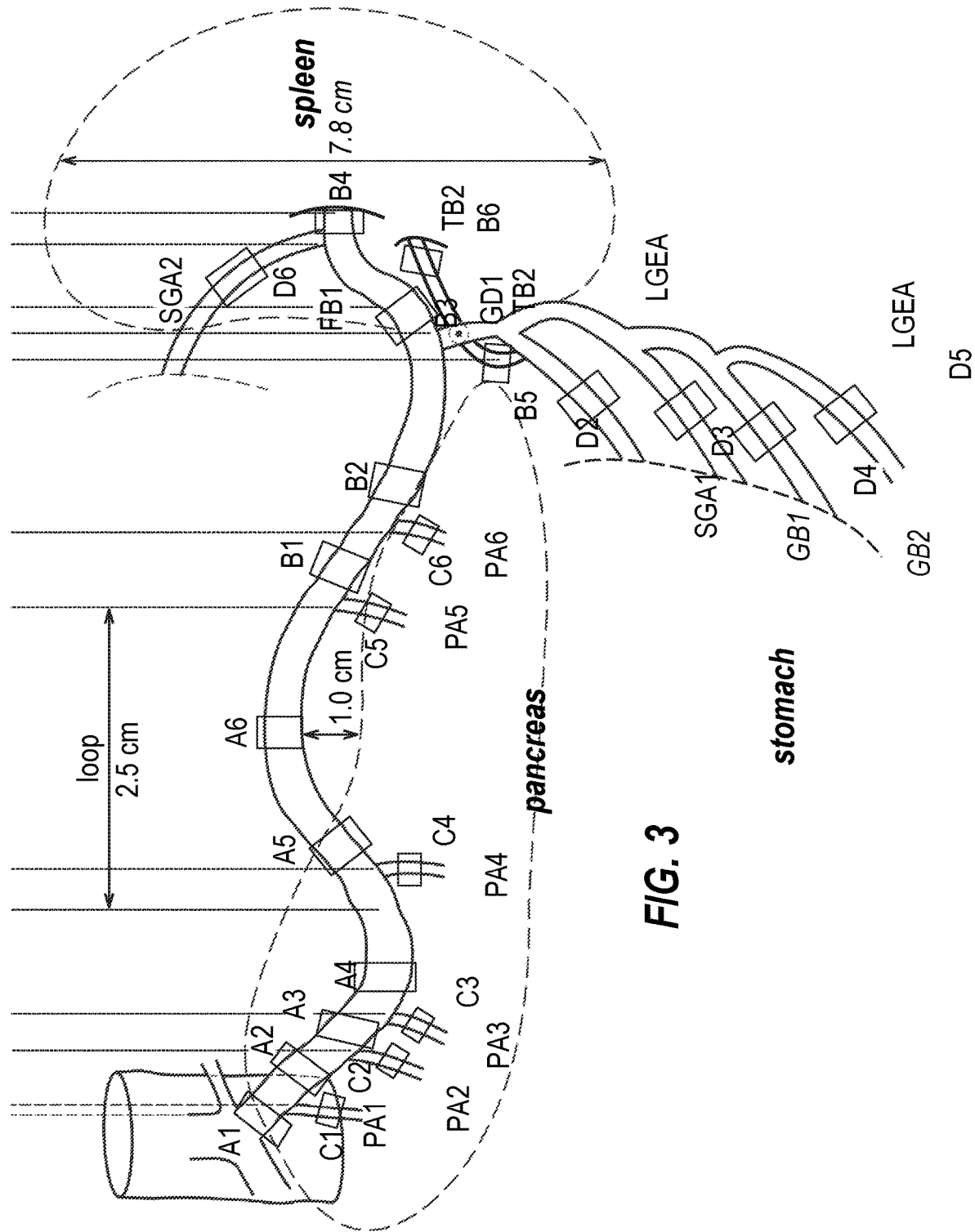
FIG. 3 shows a schematic overview of the splenic artery (SA) and its branches, including the SGA and the LGEA, in relation to the pancreas and the spleen. This images was created to serve as a schematic support for branching pattern, sample location, distances and diameters, and does not represent realistic dimension.

All six cadavers presented a single LGEA. The LGEA emerged as a branch directly from the SA in two out of six cadavers and from a lower terminal branch (LTB) in four out of six cadavers. Table 1 shows a summary of the collected quantitative data on dissection parameters concerning the LGEA of each cadaver, followed by the average value. The average diameter of the proximal LGEA was 0.2 cm (ranging from 0.15-0.28 cm), which slightly reduced during its course in the greater omentum. The average diameter of the SA before the branching LGEA was 0.31 cm (0.2-0.5). On average, the LGEA originated 9.43 cm (8.1-12.5) from the origin of the SA. While continuing its course in the greater omentum, the LGEA gave off branches to the stomach (gastric branches (GBs)) and to the greater omentum. The LGEA was mostly closely related with surrounding adipose tissue and connective tissue, but again relatively easily dissected from these tissues. FIG. 3 is a schematic representation of arteries going to the spleen, including the LGEA, in one of the cadavers.

TABLE 1

Quantitative data on dissection parameters concerning the LGEA and adjacent nerve bundles of each cadaver, followed by the average value.

| | Cadaver number | | | | | | |
|---|---|---|---|---|---|---|---|
| | III | IV | VII | VIII | IX | X | Average |
| Origin | LTB | LTB | SA | SA | LTB | LTB | |
| Distance from origin SA (cm) | 8.5 | 12.5 | 9.5 | 8.1 | 8.5 | 9.5 | 9.43 (81-12.5) |

TABLE 1-continued

Quantitative data on dissection parameters concerning the LGEA and adjacent nerve bundles of each cadaver, followed by the average value.

| | Cadaver number | | | | | | |
|---|---|---|---|---|---|---|---|
| | III | IV | VII | VIII | IX | X | Average |
| Diameter | 0.18 | 0.15 | 0.22 | 0.24 | 0.21 | 0.28 | 0.21 (1537-2772) |
| Diameter SA before LGEA (cm) | 0.25 | 0.2 | 0.5 | 0.4 | 0.2 | 0.3 | 0.21 (0.2-0.5) |
| Diameter of nerve bundles (μm) | 53 (47-59) | 51 (14-89) | 80 (17-214) | 62 (23-145) | 46 (25-97) | 44 (19-86) | 56 (14-214) |

As shown in Table 1, the average amount of nerve bundles around the LGEA is 7 (ranging from 3 to 11 nerve bundles), and the average diameter of nerve bundles around the LGEA is 56 μm (ranging from 14-214 μm).

Figure 4B:
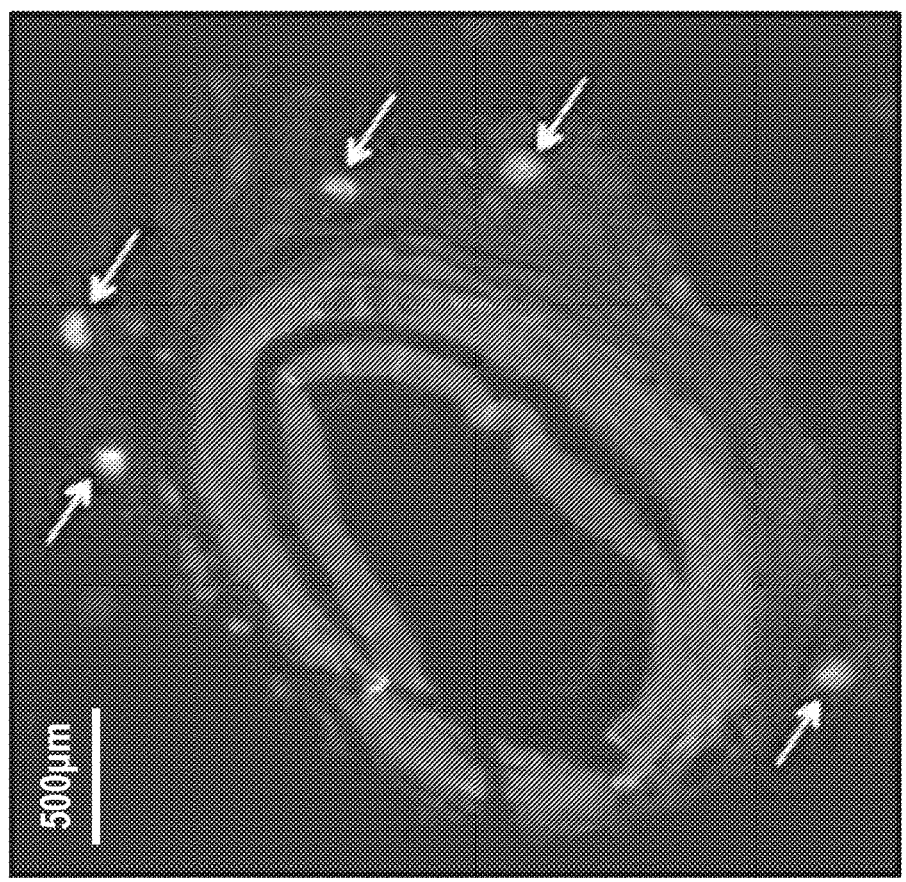
FIGS. 4A and 4B are fluorescent tile images of LGEA (A) and SGA (B) samples of cadaver III. The arrows indicate nerve bundles (5).
Figure 4A:
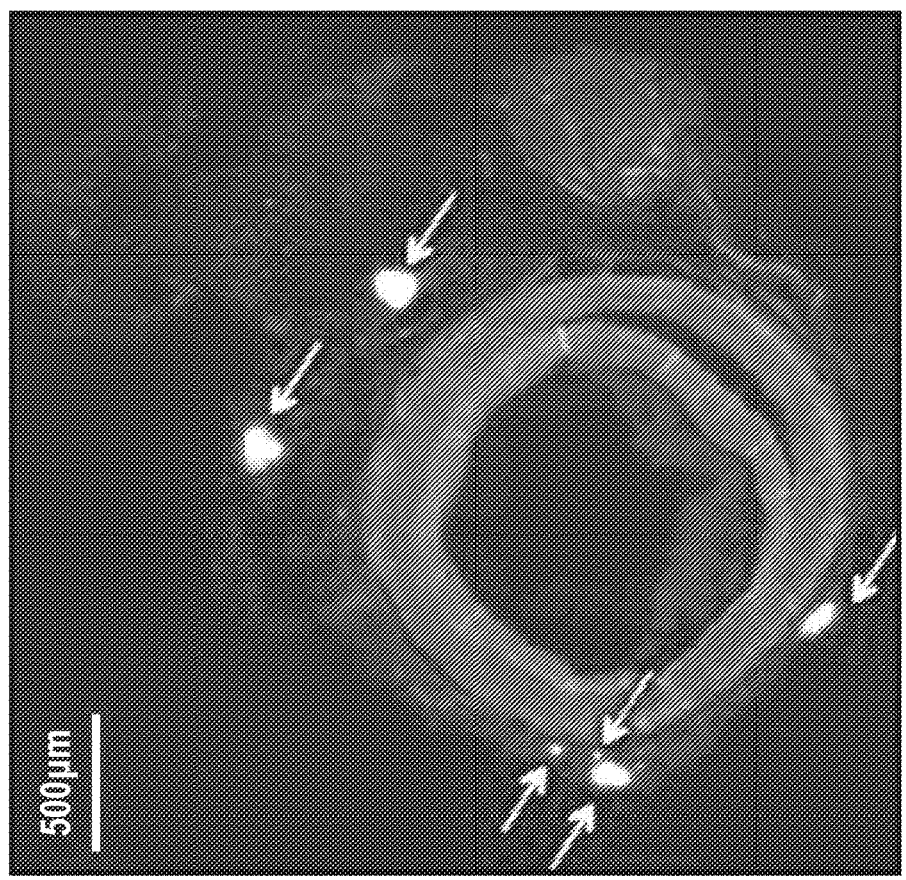
Figure 5:
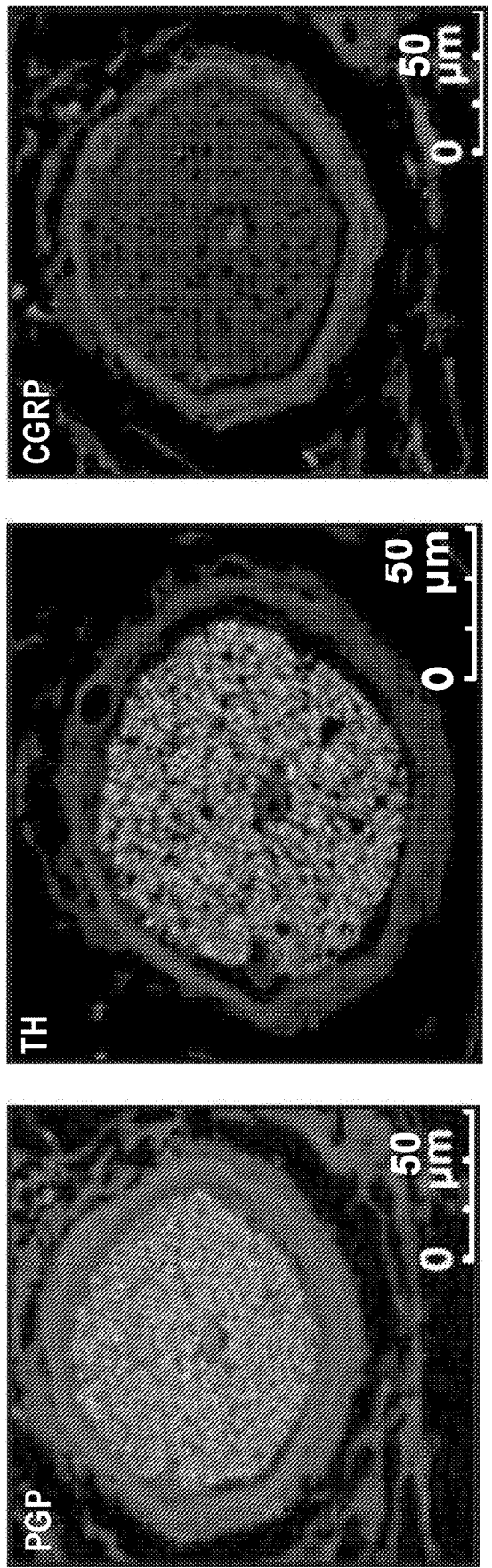
FIG. 5 is a fluorescent tile images of the LGEA and five surrounding nerves. PGP: Protein Gene Product 9.5, which is a general nerve marker. CGRP: Calcitonin gene-related peptide, which is a sensory marker. TH: tyrosine hydroxylase which is a sympathetic nerve marker.

FIG. 4A shows an exemplary tile scan of the LGEA sample with surrounding 5TH-IR nerve bundles. FIG. 5 shows that the nerves where mainly tyrosine hydroxylase (TH) positive indicating that the nerves were mainly sympathetic. No sensory, afferent, nerves were observed (absence of CGRP staining).

Short Gastric Arteries (SGAs) and the Adjacent Nerves

The average amount of SGAs branching from the SA was 3.33 (ranging from 1 to 6SGAs). Table 2 shows a summary of the collected quantitative data on dissection parameters concerning the SGAs of each cadaver, followed by the average value. The average diameter of the SGAs was 0.15 cm (ranging from 0.08-0.4 cm) and the average diameter of the SA before the branching SGA was 0.28 cm (0.1-0.6). They originated 10.19 cm (6.0-16.0) from the origin of the SA, but this is dependent on the length of the SA. The SGAs originated either from the SA itself, or from a terminal branch of the SA.

The most SGAs originated from the SA or a terminal branch relatively close to the hilum of the spleen and run in the gastrosplenic ligament to the stomach, but the SA also gave off early branching SGAs.

All SGAs run in the gastrosplenic ligament, but parts of the SGAs were closely related with surrounding adipose tissue and connective tissue, although in most cases relatively easily dissected from these surrounding tissues. Some white fibrous strands seemed to go with the SGAs to the stomach, which could be nerve bundles.

FIG. 4B shows an exemplary tile scan of SGA sample with surrounding give TH-IR nerve bundles. The average amount of nerve bundles around SGA is 4.6 (ranging from 1 to 8 nerve bundles). The average diameter of a nerve bundle around a SGA is about 55 μm (ranging from 12-173 μm).

TABLE 2

Quantitative data on dissection parameters concerning the SGAs and adjacent nerve bundles of each cadaver, followed by the average value.

| | III | IV | VII | VIII | IX | X | Average |
|---|---|---|---|---|---|---|---|
| Amount | 2 | 5 | 6 | 4 | 1 | 2 | 3.33 (1-6) |
| Distance from origin SA (cm) | 1: 8.5<br>2: 10.0 | 1: 8.5<br>2: 12.5<br>3: 12.5<br>4: 12.5 | 1: 8.5<br>2: 9.5<br>3: 10.5<br>4: 10.5 | 1: 6.3<br>2: 7.9<br>3: 9.7<br>4: 12.0 | 8.5 | 1: 6.0<br>2: 9.5 | 10.19 (6.0-16.0) |

TABLE 2-continued

Quantitative data on dissection parameters concerning the SGAs and adjacent nerve bundles of each cadaver, followed by the average value.

| | III | IV | VII | VIII | IX | X | Average |
|---|---|---|---|---|---|---|---|
| | | 5: 16.0 | 5: 11.9 | | | | |
| | | | 6: 12.5 | | | | |
| Diameter (cm) | 1: 0.23<br>2: 0.40 | 1: 0.14.1<br>2: 0.14<br>3: 0.15<br>4: 0.17<br>5: 0.22 | 1: 0.15<br>2: 0.1<br>3: 0.16<br>4: 0.11<br>5: 0.08<br>6: 0.08 | 1: 0.14<br>2: 0.14<br>3: 0.1 | 0.17 | 1: 0.12<br>2: 0.1 | 0.15 (0.08-4.0) |
| Diameter SA before SGA (cm) | 1: 0.25<br>2: 0.4 | 1: 0.5<br>2: 0.2<br>3: 0.2<br>4: 0.2<br>5: 0.2 | 1: 0.6<br>2: 0.5<br>3: 0.1<br>4: 0.1<br>5: 0.15<br>6: 0.3 | 1: 0.4<br>2: 0.4<br>3: 0.3<br>4: 0.25 | 0.25 | 1: 0.15<br>2: 0.15 | 0.28 (0.1-0.6) |
| Diameter of nerve bundles (µm) | 1: 143<br>2: 44 | 1: 79<br>2: 24<br>3: 63<br>4: 57<br>5: 37 | 1: 50<br>2: 73<br>3: 55<br>4: 63<br>5: 71<br>6: 32 | 1: 44<br>2: 54<br>3: 31 | 1: 59 | 1: 35<br>2: 30 | 55 |

Study 2: Modulation of the Nerves Adjacent to the LGEA and the SGAs in Pigs

The nerves adjacent to the LGEA and SGAs in pigs were electrically stimulated, and the level of LPS-induced TNFα in an ex vivo whole blood assay, the splenic blood flow and systolic pressure were measured.

Dissection

The SGAs and the adjacent nerves were identified during gross postmortem observation and dissection in 10 Yucatan pigs. The SGA and the adjacent nerves were consistently located in the gastrosplenic ligament running from the proximal portion of the spleen to the greater curvature of the stomach. The SGAs and the adjacent nerves were commonly paired (n=8/10) and the nerves were located adjacent to the artery. The SGA originated from the cranial branch of the splenic artery (in all specimens).

The LGEA and the adjacent nerves were identified and isolated in 7 Yucatan pigs. The LGEA and the adjacent nerves were consistently located in a ligament that course between the distal spleen and the greater curvature of the stomach. The LGEA originated from the distal splenic artery along the hilum of the spleen (all specimens).

Figure 6A:
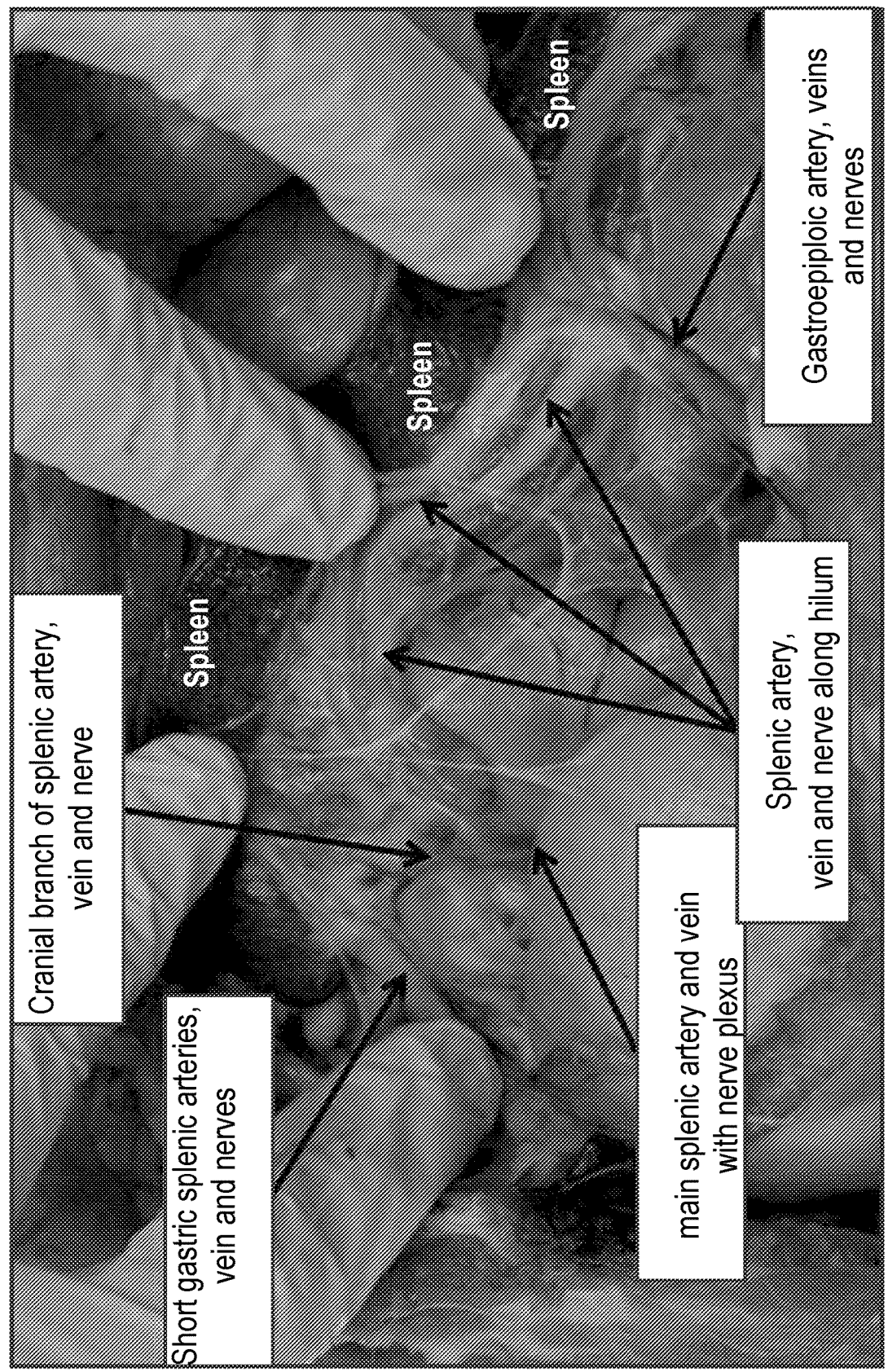
FIGS. 6A and 6B are images of gross anatomy of SG and GE artery, vein, and nerves in Yucatan pigs.
Figure 6B:
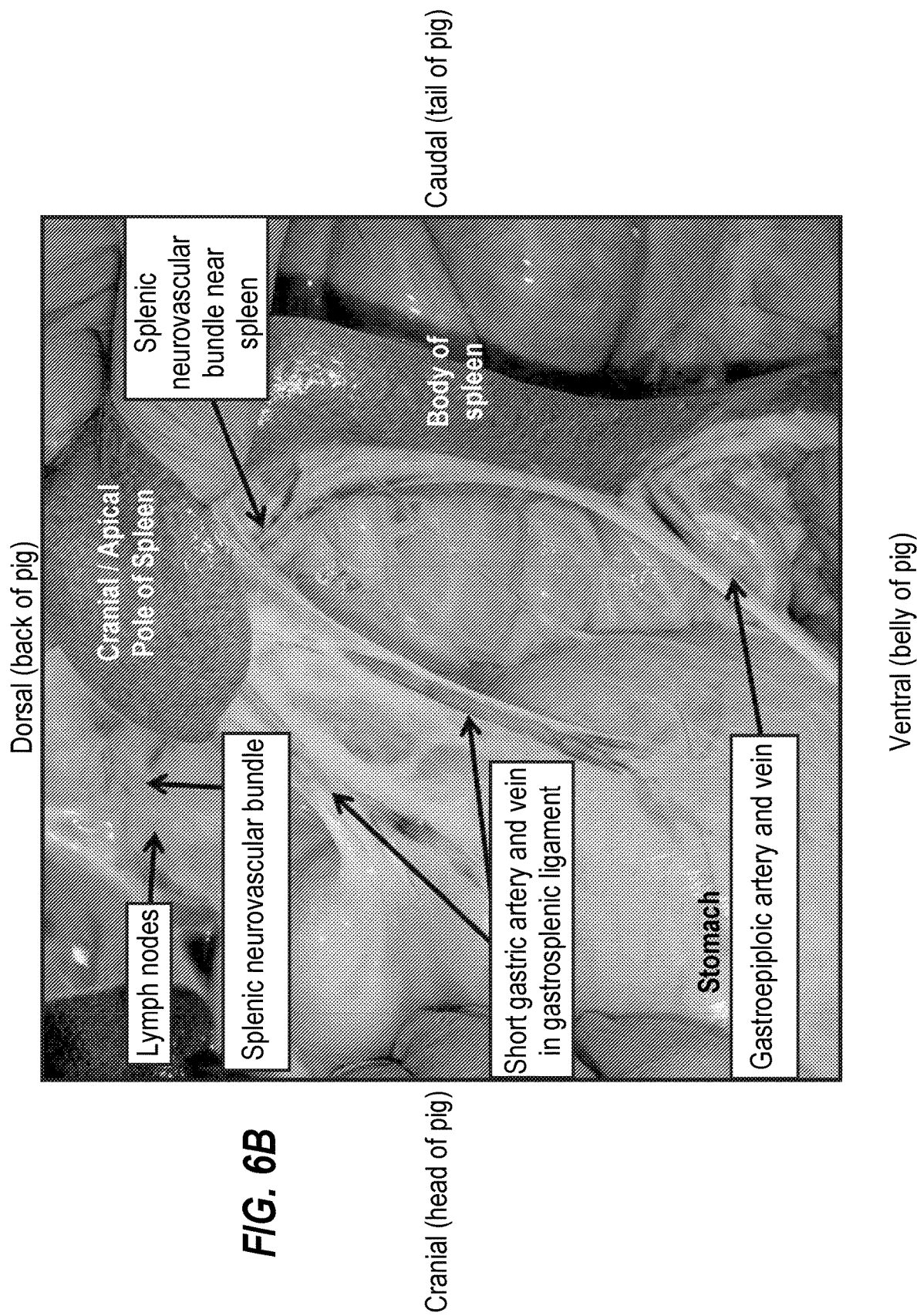

Gross anatomy of the SG and the LGE arteries, veins and nerves in the Yucatan pigs is shown in FIGS. 6A and 6B.

Histology

Initial histology from yucatan pigs (n=2, additional samples and TH pending) suggested that 2-3 nerves ranging from 100-150 microns course adjacent to the SGAs, which are approximately 200-400 microns in diameter. This is shown in FIG. 7.

Stimulation of the Nerves Adjacent to the SGAs

Figure 8A:
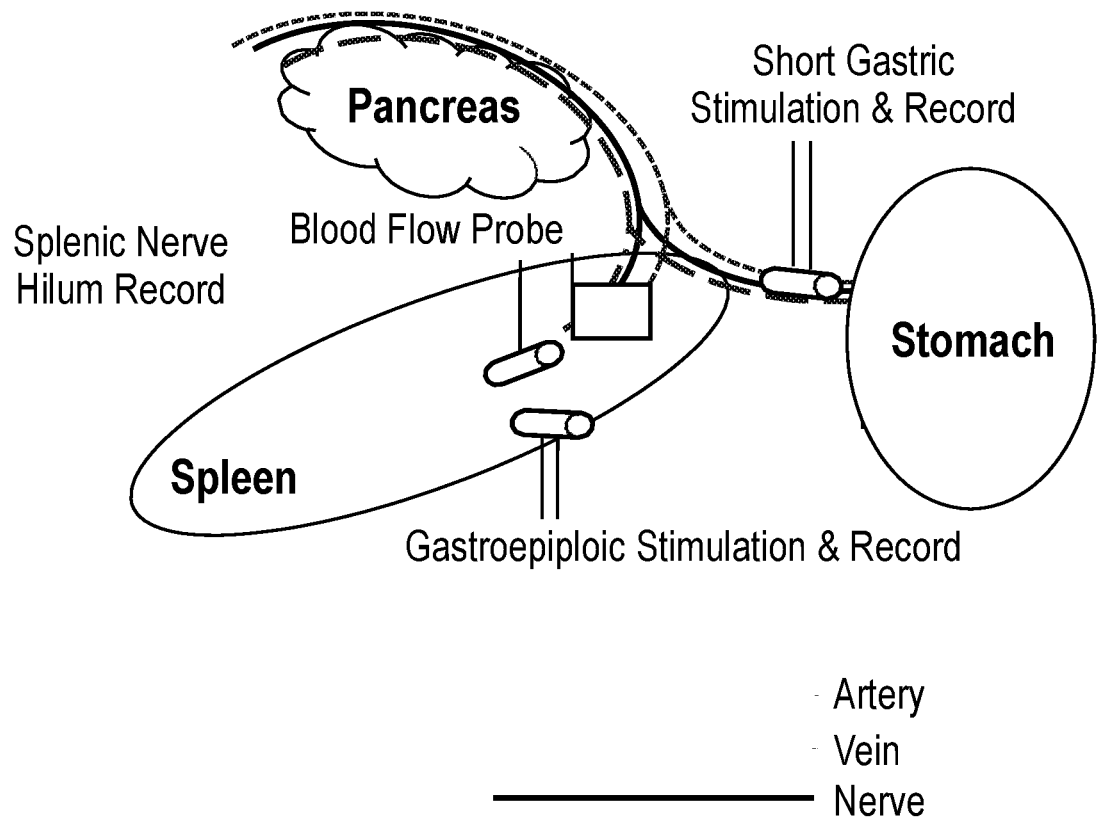
FIG. 8A is a diagram showing the locations of the cuff-electrodes around the SGA and LGEA in Yucatan pigs for stimulation and recording.
Figure 8B:
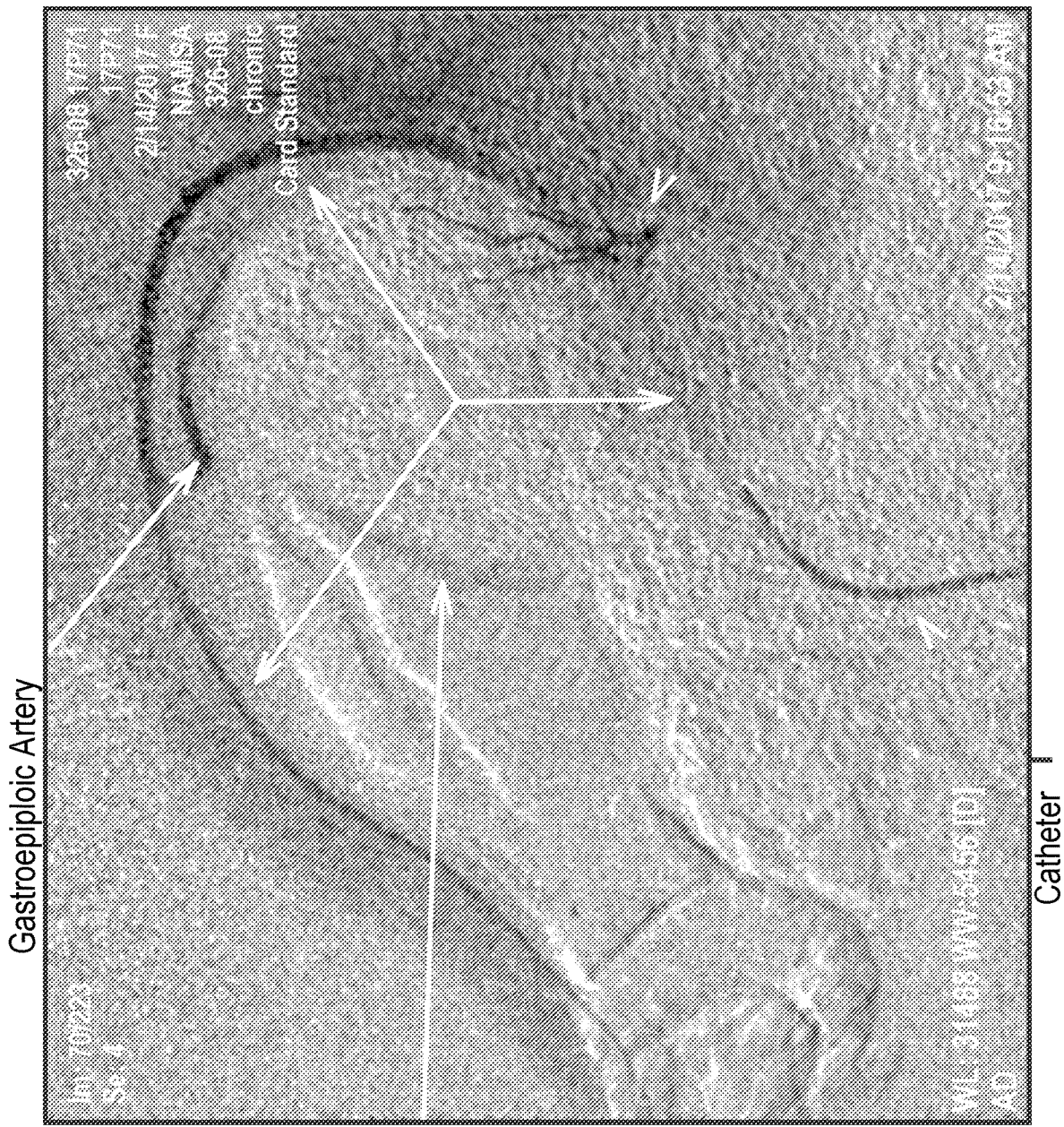
FIGS. 8B and 8C are contrast angiography of the pig spleen showing the locations of these cuff-electrodes.
Figure 8C:
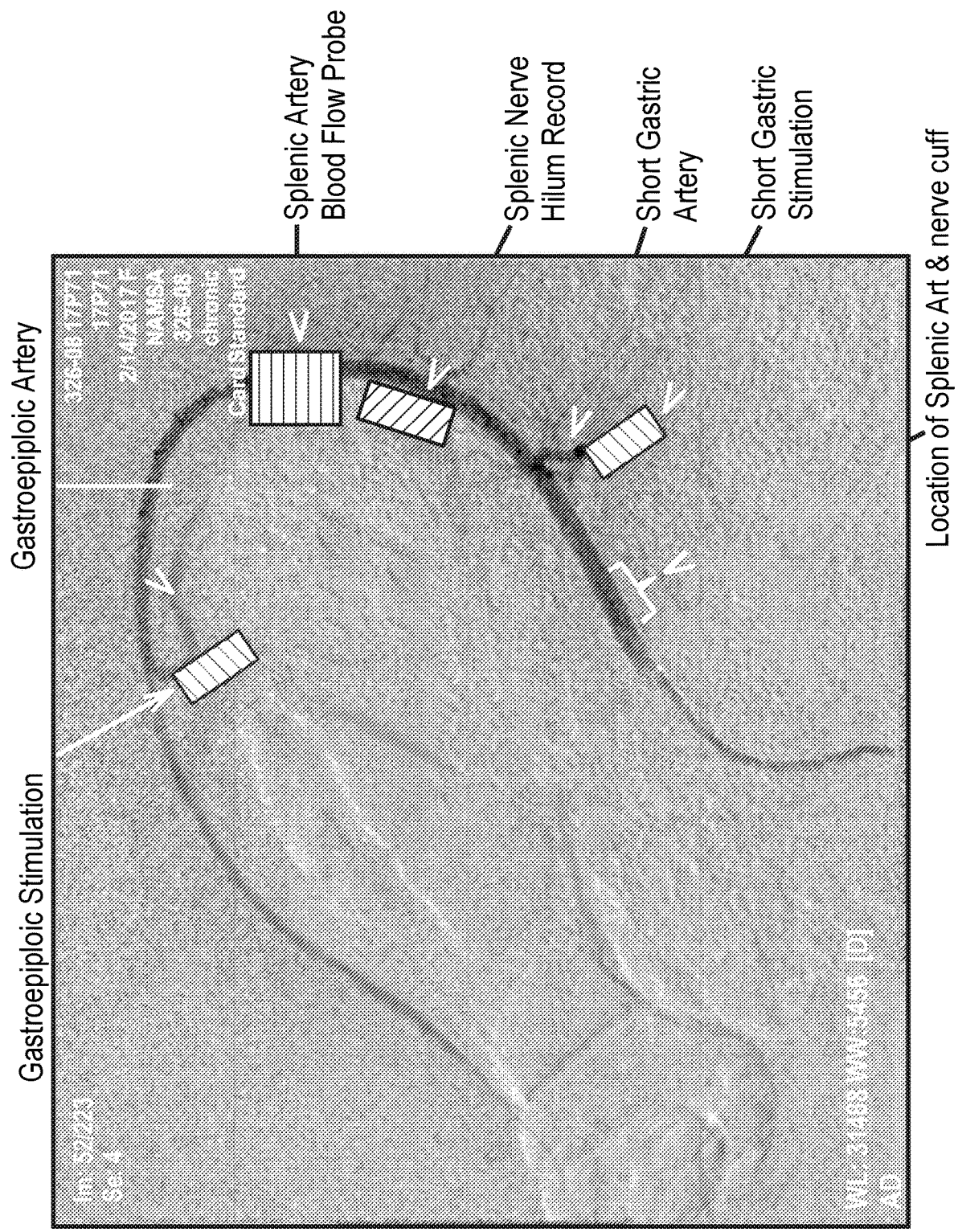

CorTec O-ring cuffs (bipolar; 800-2000 µm) of appropriate size were used to place around both the nerve adjacent to the SGA and the SGA (N=6). See FIGS. 8A, 8B and 8C for the cuff locations.

The stimulation parameters used were a current amplitude between 4-14 mA, a frequency of 10 Hz of 200 µS. The stimulation was performed for 1 minute. Stimulation parameters not optimized.

Stimulation of the Nerves Adjacent to the LGEA

CorTec O-ring cuffs (bipolar; 400-800 µm) of appropriate size were used to place around the GE nerve (no artery) (N=3). See FIGS. 8A, 8B and 8C for the cuff locations.

The stimulation parameters used were a current amplitude between 4-14 mA, a frequency of 10 Hz of 200 pS. The stimulation was performed for 1 minute. Stimulation parameters not optimized.

Results

The following measurements were performed: LPS-induced TNF production at baseline prior to stimulation and then 30, and 60 minute after stimulation, splenic arterial blood flow, systolic blood pressure, and Compound Action Potentials (CAPs; n=3)) at the level of the hilum of the spleen.

The responses following the stimulation of the nerves adjacent to the SGAs are shown in FIG. 9.

Figure 9A:
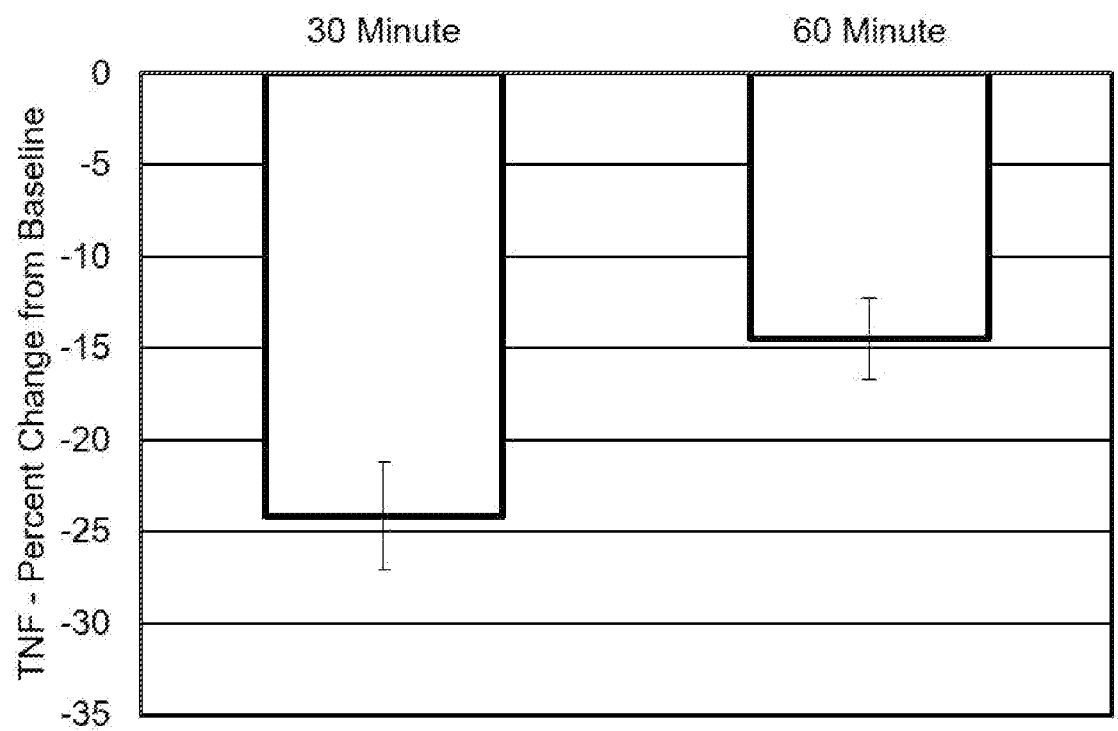
FIG. 9 shows, in FIG. 9A, the percentage change of serum level of TNFα following LPS challenge, in FIG. 9B, systolic arterial blood pressure (SAP) and splenic arterial blood flow (SpABF), and, in FIG. 9C compound action potentials (CAPs) observed in the level of splenic hilum (n=6) following stimulation of the nerves surrounding the SGA in Yucatan pigs. The A-range shows the region of A-fiber action potentials and the C-range shows the region of C-fiber action potentials. M is the marker for the start of stimulation and X is a mark from the start of stimulation at which the peak on the neurogram is measured.
Figure 9C:
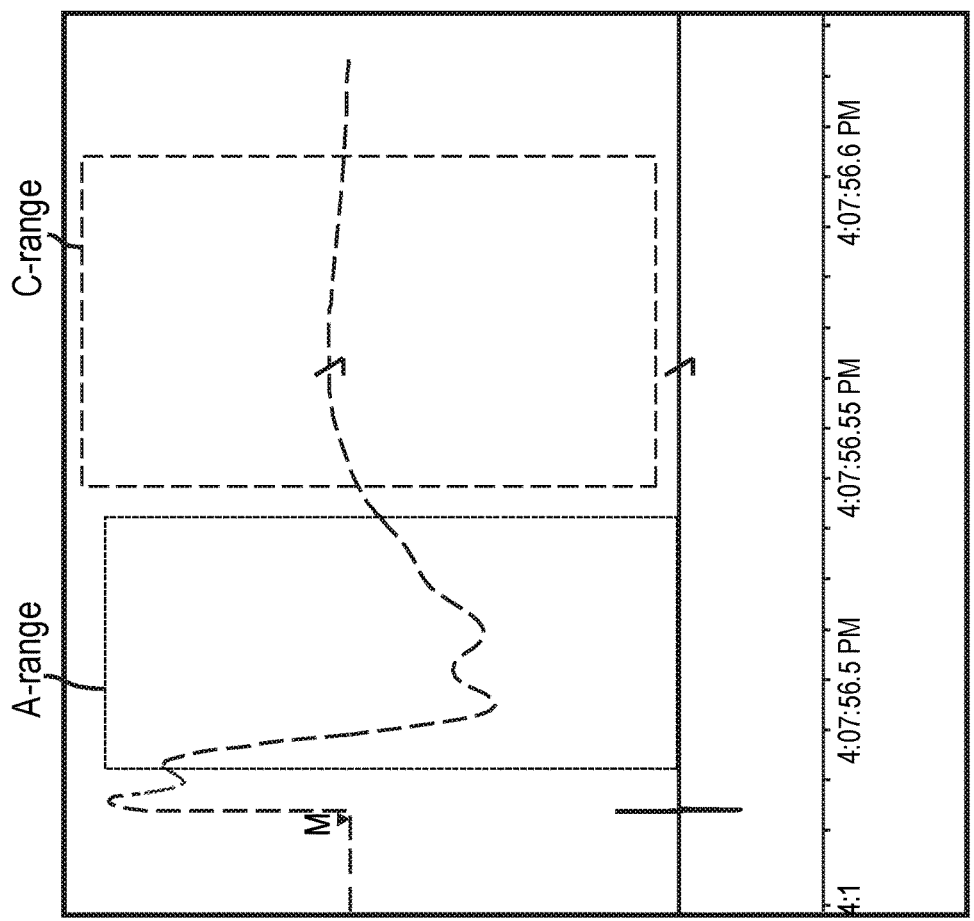
Figure 9B:
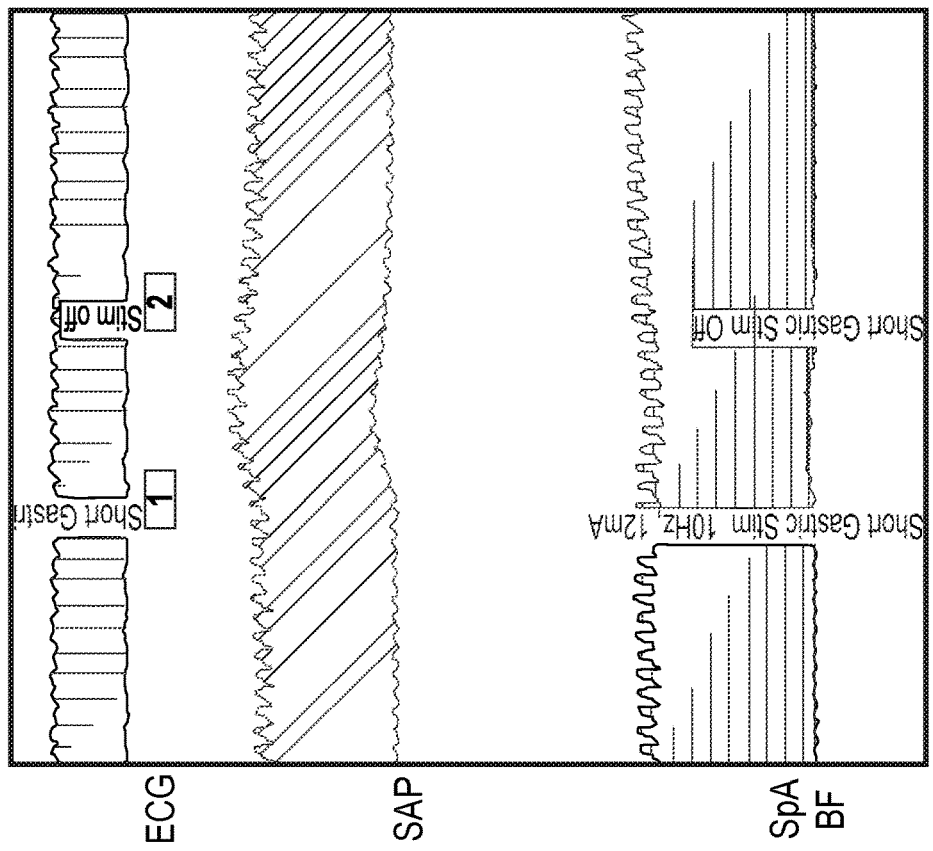

After stimulation, a reduction of approximately 24% after 30 min and 15% after 60 min compared to base line was seen in LPS-induced TNF release in a whole blood assay (see FIG. 9A). Splenic arterial blood flow (SpABF) decreased by 0-15% and systolic arterial blood pressure (SAP) increased in by 0-15% during SG stimulation (see FIG. 9B). CAPs were observed in the level of splenic hilum (see FIG. 9C, n=3).

The responses following the stimulation of the nerves adjacent to the LGEA are shown in FIG. 10.

Figure 10A:
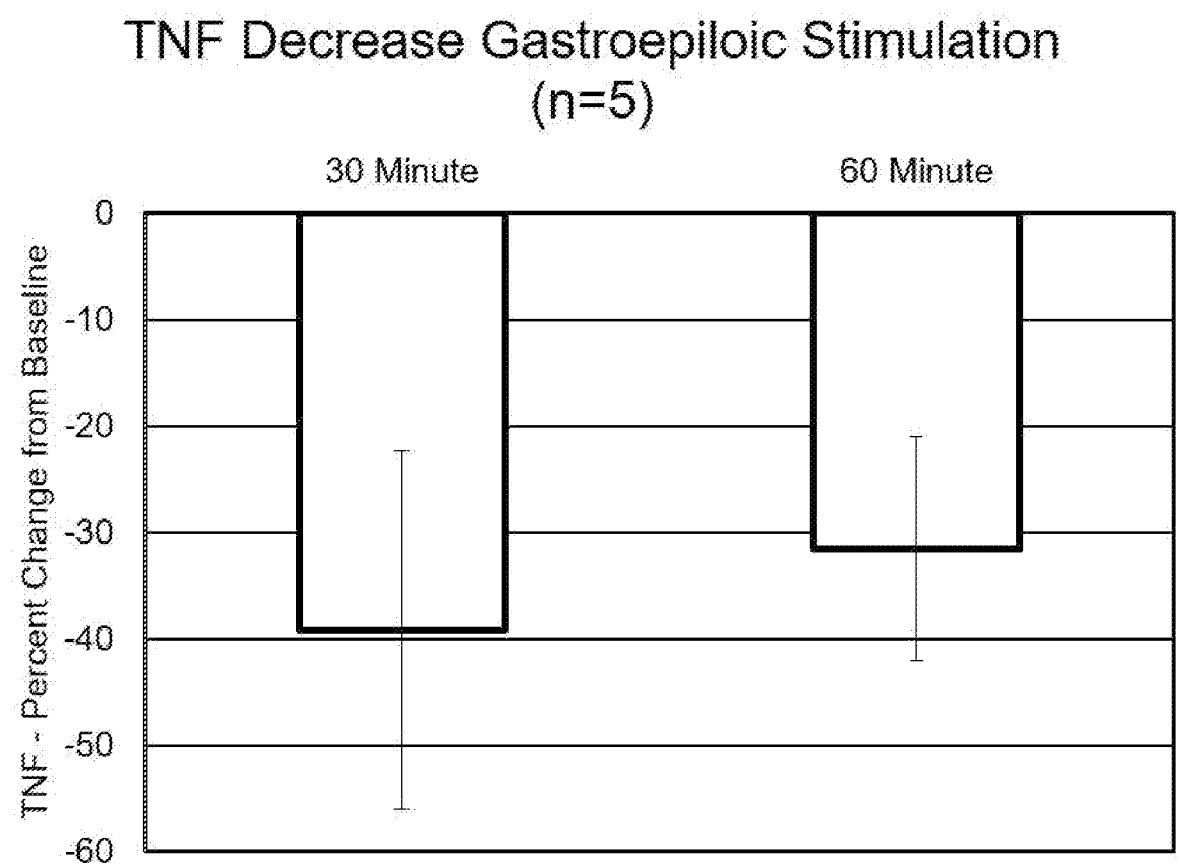
FIG. 10 shows, in FIG. 10A, the percentage change of serum level of TNFα following LPS challenge, in FIG. 10B, systolic arterial blood pressure (SAP), splenic arterial blood flow (SpABF), and neural activity recorded in the splenic nerve at the hilum, and in FIG. 10C, compound action potential (CAP) observed in the level of splenic hilum (n=5) following stimulation of the nerves adjacent to LGEA in Yucatan pigs. The A-range shows the region of A-fiber action potentials and the C-range shows the region of C-fiber action potentials. X is a mark from the start of stimulation at which the peak on the neurogram is measured.
Figure 10C:
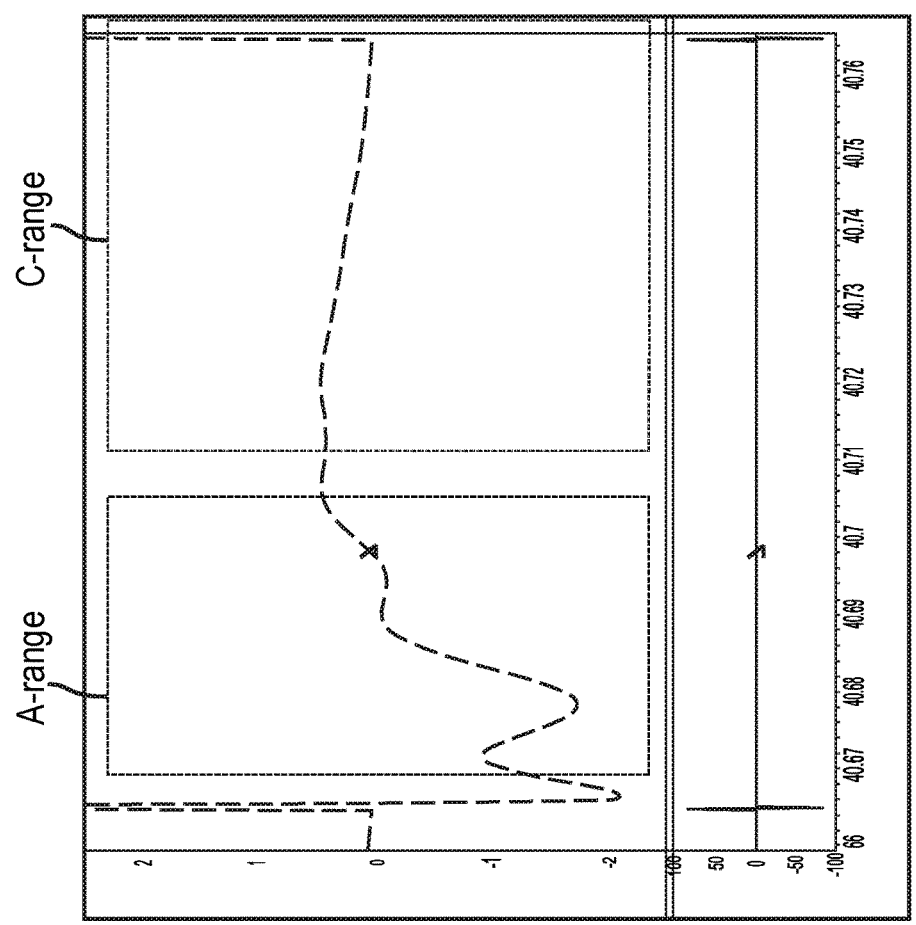
Figure 10B:
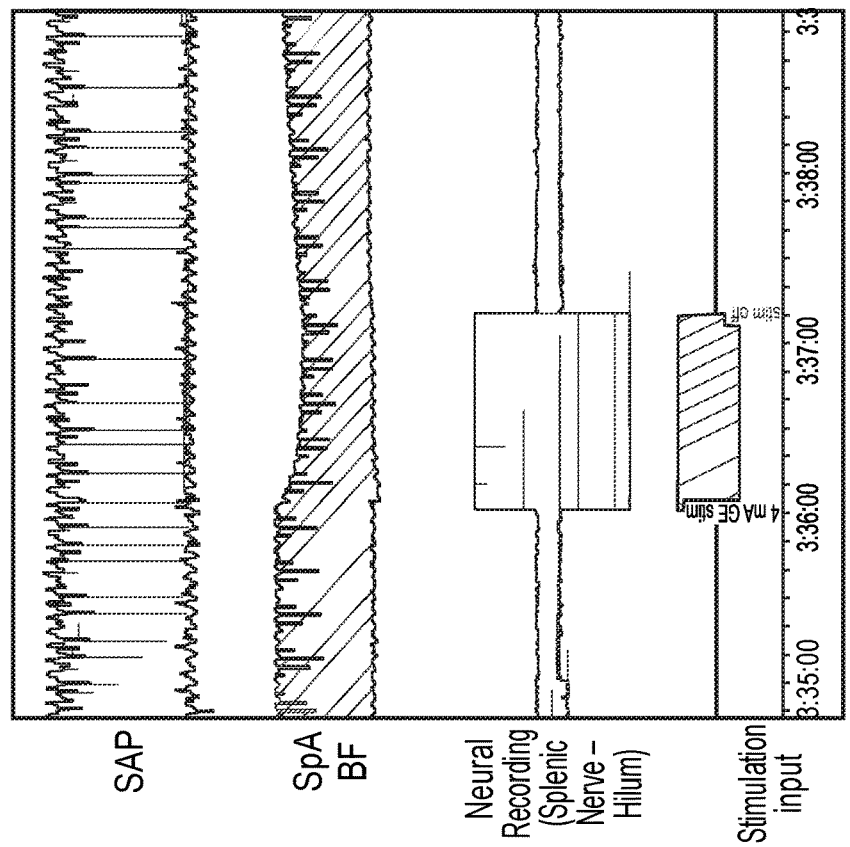
Figure 11:
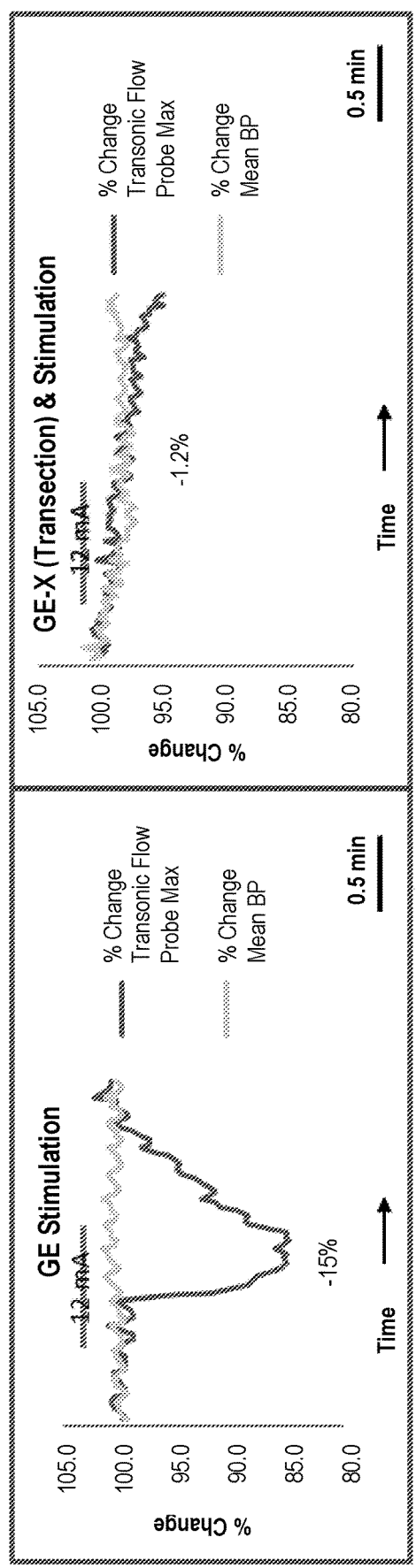
FIG. 11 shows a decrease in splenic artery blood flow in all animals and that denervation abolished stimulation induced decrease in splenic blood flow. More specifically.

After stimulation, a reduction of approximately 40% after 30 min and 32% after 60 min compared to base line was seen in LPS-induced TNF release in a whole blood assay (see FIG. 10A). Splenic arterial blood flow (SpABF) decreased consistently by 10% and systolic arterial blood pressure (SAP) changed little during SG stimulation (see FIG. 10B). Compound action potentials (CAPs) were observed in the level of splenic hilum (see FIG. 10C, n=3). Additionally cutting the nerve near the cuff abolished the decrease in splenic blood flow and CAP (n=2).

CONCLUSION

The effects of electrically stimulating the nerves adjacent to the SGAs or the LGEAs were similar to the effects of electrically stimulating the nerves adjacent to the SA. In particular, stimulating the nerves adjacent to the SGAs and LGEAs led to a decrease in LPS induced TNF, a decrease in splenic blood flow, and an increase in systolic pressure. In addition, by denervating the nerves adjacent to the LGEA it was shown that the effect was caused by a specific stimulation of the nerves and was not due to a specific current leakage.

DISCUSSION

Histological analysis of the white fibers in the human gastrosplenic ligament revealed that these white strands were no nerves, but small nerve bundles were observed using different methods of staining.

These nerves are run around the LGEA and the SGAs.

The LGEA and SGAs were visible by eye in a Yucatan pig. Usually two arteries surrounded by nerves were present in the gastrosplenic ligament. Histological analysis confirmed the presence of arteries and nerves in the gastro splenic ligament of the pig. Stimulation of the nerves adjacent to the LGEA and the nerves adjacent to the SGAs at the proximal part of the nerves near the spleen with a neural interface in acute experiments in pigs resulted in a systemic reduction in pro-inflammatory cytokines, including TNFα. These arteries therefore represent a stimulation target that is different from the splenic arterial nerve plexus and is useful for electric neuro-immunomodulation therapy in chronic inflammatory diseases.

It is more advantageous to stimulate the nerves adjacent to the LGEA and SGAs compared to the nerves adjacent to the SA. Some of the advantages are summarized as follows:

I. The nerve plexuses surrounding the LGEA and SGA are surgically easier site to access compared to the nerve plexus surrounding the SA.

II. Reduced safety issues; May represent less artery/vascular risk than encircling main splenic artery:
   a. Easily removable from the gastrosplenic ligament as needed; Loss of artery may have less severe impact. (surgical procedures exist in which the gastrosplenic ligament is removed [16]);
   b. SGA and LGEA not in proximity of pancreas; Avoids dissection adjacent to pancreas; and
   c. Surgical procedure shorter.

III. Development of neural interface is easier:
   a. Pulsation of artery minimal;
   b. Potentially an existing neuromodulation device might be used; and
   c. Patch or clip neural interface might be used.

Key Findings

I. Nerves around arteries were detected in human and porcine specimens of the gastrosplenic ligament.

II. The nerves in human and pig were similar in size and numbers.

III. Stimulation delivered using a neural interface cuff around one of the nerves and artery, of either the LGEA or SGA, resulted in a reduction in pro-inflammatory cytokines.

IV. Stimulating the nerve bundles surrounding LGEA without cuffing the artery resulted in a reduction in pro-inflammatory cytokines.

V. Sites other than main nerve plexus along SA may be sites for intervention to modulate immune responses.

VI. Effects of stimulating the nerves adjacent to the SGAs and the LGEA are similar to stimulation of nerves adjacent to the SA.

VII. More than 98% of the nerves are sympathetic efferent nerves.

VIII. SGAs and LGEA are present in 100% of the human cadavers investigated.

REFERENCES

[1] Medzhitov, Nature 454, 428-435 (24 Jul. 2008).
[2] J. M. Huston et al., J Exp Med 203, 1623.
[3] D. M. Nance, V. M. Sanders, Brain Behav Immun 21, 736.
[4] H. H. Dale, H. W. Dudley, J Physiol 68, 97.
[5] C. Cailotto et al., Neurogastroenterol Motil 24, 191.
[6] M. Rosas-Ballina, K. J. Tracey, Neuron 64, 28.
[7] G. Vida, G. Pena, E. A. Deitch, L. Ulloa J Immunol 186, 4340.
[8] B. O. Bratton et al., Exp Physiol 97, 1180.
[9] D. Martelli, S. T. Yao, M. J. McKinley, R. M. McAllen, J Physiol 592(7), 1677.
[10] D. Martelli, S. T. Yao, J. Mancera, M. J. McKinley, R. M. McAllen, Am J Physiol Regul Integr Comp Physiol 307, R1085.
[11] D. Martelli, M. J. McKinley, R. M. McAllen, Auton Neurosci. 182, 65.
[12] Koopman F A et al., Proc Natl Acad Sci USA, 19; 113(29):8284.
[13] US 2006/0287678.
[14] US 2005/0075702.
[15] US 20050075701.
[16] O'Boyle et al., 2002, Ann. Surg. 235(2):165-70.
[17] Abramson, 1962, Blood Vessels and Lympahtics (1st Ed.) New York: Academic Press.
[18] Gray, 1980, Gray's Anatomy. (P. Williams & R. Warwick, Eds.) 36th Ed. Churchill Livingsone.
[19] Sahni et al., 2003, Clin. ANA. 16(5):371-377.
[20] Kramer et al., Optogenetic pharmacology for control of native neuronal signaling proteins, 2013; 16(7):816-23.
[21] Duke et al. (2012). J. Neural Eng., 9(3):036003.

The invention claimed is:

1. A system for modulating neural activity in a subject's nerve adjacent to the left gastro epiploic artery (LGEA) and/or a subject's nerve adjacent to a short gastric artery (SGA) to produce a change in splenic arterial flow for treating an inflammatory disorder, and/or immune mediated inflammatory disease, the system comprising:
   at least one electrode, in signaling contact with the nerve, and
   a voltage or current source configured to generate at least one electrical signal to be applied to the nerve via the at least one electrode such that a charge density per phase applied to the nerve modulates the neural activity of the nerve to produce a change in the splenic arterial flow and further produce a change in a physiological parameter associated with the inflammatory disorder and/or immune mediated inflammatory disease in the subject,
   wherein the change in the physiological parameter is one or more of the group consisting of: a reduction in a pro-inflammatory cytokine, an increase in an anti-inflammatory cytokine, an increase in a catecholamine, a change in an immune cell population, a change in an immune cell surface co-stimulatory molecule, a reduction in a factor involved in the inflammation cascade, a change in the level of an immune response mediator, and a decrease in splenic blood flow.

2. The system of claim 1, wherein the system modulates neural activity in a nerve adjacent to the LGEA, and the at least one electrode is placed on or around both the nerve adjacent to the LGEA and the LGEA.

3. The system of claim 1, wherein the system modulates neural activity in a nerve adjacent to the LGEA, wherein the at least one electrode is placed on or around the nerve adjacent to the LGEA.

4. The system of claim 1, wherein the system modulates neural activity in a nerve adjacent to a SGA, and the at least one electrode is placed on or around both the nerve adjacent to the SGA and the SGA.

5. The system of claim 1, wherein the system modulates neural activity in a nerve adjacent to a SGA, and the at least one electrode is placed on or around the nerve adjacent to the SGA.

6. The system of claim 1, wherein the at least one electrical signal comprises one or more pulse trains, each comprising a plurality of square pulses.

7. The system of claim 6, wherein the pulses are biphasic charge-balanced pulses.

8. The system of claim 6, wherein the pulses are monophasic pulses.

9. The system of claim 1, wherein the voltage or current source is configured to apply the at least one electrical signal episodically.

10. The system of claim 9, wherein each episode comprises between 120 and 3000 pulses of the signal.

11. The system of claim 1, wherein the voltage or current source is configured to apply the signal periodically.

12. The system of claim 1, comprising a detector configured to:
detect one or more signals indicative of one or more physiological parameters; determine from the one or more signals one or more physiological parameters; determine the one or more physiological parameters indicative of worsening of the physiological parameter; and causing the signal to be applied to the nerve via the at least one electrode,
wherein the physiological parameter is one or more of the group consisting of: the level of a pro-inflammatory or an anti-inflammatory cytokine, the level of a catecholamine, the level of an immune cell population, the level of an immune cell surface co-stimulatory molecule, the level of a factor involved in the inflammation cascade, the level of an immune response mediator, and splenic blood flow.

13. The system of claim 12, further comprising a memory configured to store data pertaining to the physiological parameters in a healthy subject, wherein determining the one or more physiological parameters indicative of worsening of the physiological parameter comprises comparing the one or more physiological parameters with the data.

14. The system of claim 1, comprising a communication subsystem configured to receive a control signal from a controller and, upon detection of said one or more control signals, cause the electrical signal to be applied to the nerve via the at least one electrode.

15. A method of reducing inflammation in a subject by reversibly modulating neural activity of the subject's nerve adjacent to the LGEA and/or the subject's nerve adjacent to a SGA, comprising: (i) implanting in the subject a system of claim 1; positioning the at least one electrode in signaling contact with the nerve; and (iii) activating the system.

16. The method of claim 15, wherein the method is for treating an inflammatory disorder.

17. A method for treating an inflammatory disorder and/or immune mediated inflammatory disease, comprising:
applying an electrical signal to a subject's nerve adjacent to the left gastro epiploic artery (LGEA) and/or a subject's nerve adjacent to a short gastric artery (SGA) via at least one electrode, in signaling contact with the nerve, such that the signal reversibly modulates neural activity of the nerve to produce a change in splenic arterial flow and to produce a change in a physiological parameter associated with the inflammatory disorder and/or immune mediated inflammatory disease, in the subject,
wherein the change in the physiological parameter is one or more of the group consisting of: a reduction in a pro-inflammatory cytokine, an increase in an anti-inflammatory cytokine, an increase in a catecholamine, a change in an immune cell population, a change in an immune cell surface co-stimulatory molecule, a reduction in a factor involved in the inflammation cascade, a change in the level of an immune response mediator, and a decrease in splenic blood flow.

* * * * *